(12) United States Patent
Bryan et al.

(10) Patent No.: US 11,406,558 B2
(45) Date of Patent: Aug. 9, 2022

(54) REDUCING BRAIN INJURY BY LIMITING BRAIN MOTION DURING SUDDEN DECELERATION OR ACCELERATION OF THE HEAD

(71) Applicant: PreActive Technologies Inc., Kirkland, WA (US)

(72) Inventors: Vincent E. Bryan, Quincy, WA (US); Randal P. Ching, Seattle, WA (US); Daniel Reed Baker, Seattle, WA (US)

(73) Assignee: PreActive Technologies Inc., Kirkland, WA (US)

( * ) Notice: Subject to any disclaimer, the term of this patent is extended or adjusted under 35 U.S.C. 154(b) by 880 days.

(21) Appl. No.: 15/467,912

(22) Filed: Mar. 23, 2017

(65) Prior Publication Data

US 2017/0304140 A1    Oct. 26, 2017

Related U.S. Application Data

(60) Provisional application No. 62/462,906, filed on Feb. 23, 2017, provisional application No. 62/496,899, (Continued)

(51) Int. Cl.
*A61B 5/00* (2006.01)
*A42B 3/04* (2006.01)
(Continued)

(52) U.S. Cl.
CPC ......... *A61H 9/0078* (2013.01); *A42B 3/0406* (2013.01); *A42B 3/046* (2013.01); (Continued)

(58) Field of Classification Search
CPC ..... A42B 3/0433; A42B 3/046; A42B 3/0486; A42B 3/122; A61B 5/11; A61B 5/6803; (Continued)

(56) References Cited

U.S. PATENT DOCUMENTS

| 3,735,398 A | 5/1973 | Ross |
| 4,907,602 A * | 3/1990 | Sanders ............... A61N 1/3601 |
| | | 607/134 |

(Continued)

FOREIGN PATENT DOCUMENTS

| EP | 3171768 A1 | 5/2017 |
| EP | 3302691 B1 | 7/2019 |

(Continued)

OTHER PUBLICATIONS

Porth, CJ, et al. "The Valsalva maneuver: mechanisms and clinical implications." Heart Lung, Sep. 13, 1984 (Year: 1984).*

(Continued)

*Primary Examiner* — Bradley H Philips
*Assistant Examiner* — Savannah L Gabriel
(74) *Attorney, Agent, or Firm* — Fenwick & West LLP

(57) ABSTRACT

A brain injury reduction system provides a protective measure that temporarily or decreases venous drainage out of the intracranial compartment during or immediately before and during a sudden change in acceleration of an individual's head. Specifically, a wearable helmet or other wearable structure of the brain injury reduction system detects an impending collision and determines whether a protective measure is needed. If so, one or more actuation devices provides the protective measure to reduce venous drainage through one or both of the internal jugular veins or paravertebral venous plexus. A first actuation device stimulates a gag reflex or valsalva-like maneuver to reduce venous drainage through the paravertebral venous plexus. A second actuation device can physically compress the internal jugular veins. Thus, the brain injury reduction system minimizes the detrimental impact that may occur due to the sudden change in acceleration of the individual's head.

26 Claims, 9 Drawing Sheets

Related U.S. Application Data filed on Nov. 1, 2016, provisional application No. 62/391,302, filed on Apr. 25, 2016.

(51) Int. Cl.
  *A61H 9/00* (2006.01)
  *A61N 1/00* (2006.01)
  *A61N 1/04* (2006.01)
  *A61N 1/36* (2006.01)
  *A61B 5/11* (2006.01)
  *A61B 17/135* (2006.01)

(52) U.S. Cl.
  CPC .............. *A42B 3/0433* (2013.01); *A61B 5/11* (2013.01); *A61B 5/6803* (2013.01); *A61B 5/7267* (2013.01); *A61N 1/00* (2013.01); *A61N 1/0456* (2013.01); *A61N 1/0484* (2013.01); *A61N 1/36014* (2013.01); *A61B 5/4836* (2013.01); *A61B 17/135* (2013.01); *A61H 2201/5058* (2013.01)

(58) Field of Classification Search
  CPC ................ A61B 5/4064; A61B 5/6814; A61B 2562/0219; A61N 1/0456; A61N 1/0484; A61N 1/36014; A61N 1/0551–0558; A61N 1/3605–3606; A61N 1/36; A61N 1/321
  See application file for complete search history.

(56) References Cited

U.S. PATENT DOCUMENTS

| | | | |
|---|---|---|---|
| 5,016,647 A | 5/1991 | Sanders | |
| 5,038,796 A | 8/1991 | Axelgaard et al. | |
| 5,048,522 A | 9/1991 | Petrofsky | |
| 5,397,337 A * | 3/1995 | Jaeger | A61N 1/3601 |
| | | | 607/62 |
| 5,467,766 A | 11/1995 | Ansite et al. | |
| 5,546,609 A | 8/1996 | Rush | |
| RE36,120 E * | 3/1999 | Karell | A61F 5/566 |
| | | | 128/848 |
| 5,897,579 A | 4/1999 | Sanders | |
| 6,213,960 B1 * | 4/2001 | Sherman | A61N 1/39044 |
| | | | 601/41 |
| 6,594,614 B2 | 7/2003 | Studt et al. | |
| 7,890,178 B2 * | 2/2011 | Testerman | A61N 1/36017 |
| | | | 607/48 |
| 7,954,900 B2 | 6/2011 | Shantha et al. | |
| 8,172,769 B2 | 5/2012 | Lenhardt et al. | |
| 8,588,919 B2 | 11/2013 | Li | |
| 8,702,516 B2 | 4/2014 | Bentley et al. | |
| 9,226,707 B2 | 1/2016 | Huang | |
| 9,272,139 B2 | 3/2016 | Hamilton et al. | |
| 9,474,898 B2 | 10/2016 | Gozani et al. | |
| 9,616,234 B2 | 4/2017 | Harry et al. | |
| 9,884,178 B2 | 2/2018 | Bouton et al. | |
| 9,884,179 B2 | 2/2018 | Bouton et al. | |
| 10,001,346 B2 | 6/2018 | Augustine et al. | |
| 10,195,010 B2 | 2/2019 | Sanders | |
| 10,285,934 B1 | 5/2019 | Sharma et al. | |
| 10,335,396 B2 | 7/2019 | Nemechek | |
| 2003/0182040 A1 | 9/2003 | Davidson | |
| 2004/0181161 A1 * | 9/2004 | Addington | A61B 5/08 |
| | | | 600/529 |
| 2005/0283205 A1 | 12/2005 | Lee et al. | |
| 2007/0293926 A1 | 12/2007 | Dunlay et al. | |
| 2008/0215128 A1 | 9/2008 | Rainey et al. | |
| 2010/0063736 A1 | 3/2010 | Hoetzer | |
| 2010/0303289 A1 | 12/2010 | Polzin et al. | |
| 2010/0312139 A1 | 12/2010 | Dash et al. | |
| 2011/0082514 A1 | 4/2011 | Libbus et al. | |
| 2011/0089725 A1 | 4/2011 | Shantha et al. | |
| 2011/0226264 A1 * | 9/2011 | Friedman | A61B 1/267 |
| | | | 128/848 |
| 2013/0197321 A1 * | 8/2013 | Wilson | A61B 7/008 |
| | | | 600/301 |
| 2013/0274615 A1 | 10/2013 | Ben-Ari et al. | |
| 2013/0296751 A1 * | 11/2013 | Martin | A63B 21/0085 |
| | | | 601/148 |
| 2013/0310909 A1 | 11/2013 | Simon et al. | |
| 2014/0142616 A1 | 5/2014 | Smith | |
| 2014/0236058 A1 * | 8/2014 | Lee | A61B 17/1355 |
| | | | 601/84 |
| 2014/0276278 A1 * | 9/2014 | Smith | A61B 5/6804 |
| | | | 601/133 |
| 2014/0323921 A1 * | 10/2014 | Huang | A61B 5/4064 |
| | | | 600/587 |
| 2014/0343599 A1 | 11/2014 | Smith et al. | |
| 2014/0371545 A1 | 12/2014 | Ben-Ari et al. | |
| 2015/0120007 A1 | 4/2015 | Guez et al. | |
| 2015/0321000 A1 | 11/2015 | Rosenbluth et al. | |
| 2015/0335288 A1 | 11/2015 | Toth et al. | |
| 2016/0000367 A1 | 1/2016 | Lyon | |
| 2016/0310730 A1 * | 10/2016 | Martins | A61M 16/0051 |
| 2017/0006931 A1 | 1/2017 | Guez et al. | |
| 2017/0231490 A1 | 8/2017 | Toth et al. | |
| 2017/0304140 A1 | 10/2017 | Bryan et al. | |
| 2018/0001086 A1 | 1/2018 | Bartholomew et al. | |
| 2018/0008155 A1 | 1/2018 | Melker et al. | |
| 2018/0154140 A1 | 6/2018 | Bouton et al. | |
| 2018/0178008 A1 | 6/2018 | Bouton et al. | |
| 2018/0178013 A1 | 6/2018 | Bouton et al. | |
| 2018/0214117 A1 | 8/2018 | Oura | |
| 2018/0353086 A1 | 12/2018 | Turner et al. | |
| 2019/0001126 A1 | 1/2019 | Evans et al. | |
| 2019/0001127 A1 | 1/2019 | Evans et al. | |
| 2019/0059495 A1 | 2/2019 | Bryan et al. | |
| 2019/0126018 A1 | 5/2019 | Browd et al. | |
| 2019/0262212 A1 | 8/2019 | Schroeder | |

FOREIGN PATENT DOCUMENTS

| | | |
|---|---|---|
| WO | WO 2011/044173 A1 | 4/2011 |
| WO | WO 2015/061663 A1 | 4/2015 |
| WO | WO 2017/087556 A1 | 5/2017 |
| WO | WO 2018/085439 A1 | 5/2018 |
| WO | WO 2018/213456 A1 | 11/2018 |

OTHER PUBLICATIONS

Dunn, T. Laurence, "Raised Intracranial Pressure" 2002, J Neurol Neurosurg Psychiatry, 73, pp. 23-27 (Year: 2002).*
Takanori, Tsujimura, et. al. "Laryngeal and tracheal afferent nerve stimulation evokes swallowing in anesthetized guinea pigs" 2013, pp. 4667-4679 (Year: 2013).*
PCT International Search Report and Written Opinion, PCT/US2017/023889, dated Jun. 16, 2017, 16 pages.
Schaller, B., "Physiology of Cerebral Venous Blood Flow: From Experimental Data in Animals to Normal Function in Humans," Brain Research Reviews, Apr. 26, 2004, vol. 46, pp. 243-260.
European Patent Office, Extended European Search Report and Opinion, EP Patent Application No. 17790057.8, dated Dec. 6, 2019, eight pages.
European Patent Office, Extended European Search Report and Opinion, EP Patent Application No. 19205341.1, dated Feb. 26, 2020, seven pages.
Prabhakar, H. et al., "Intracranial pressure changes during Valsalva Manoeuvre in Patients Undergoing a Neuroendoscopic Procedure," Minimally Invasive Neurosurgery, May 2007, pp. 98-101.
United States Office Action, U.S. Appl. No. 16/171,184, dated Nov. 9, 2021, 21 pages.

\* cited by examiner

160

REDUCING BRAIN INJURY BY LIMITING BRAIN MOTION DURING SUDDEN DECELERATION OR ACCELERATION OF THE HEAD

CROSS-REFERENCE TO RELATED APPLICATIONS

This application claims priority to U.S. Provisional Application No. 62/391,302 filed on Apr. 25, 2016, U.S. Provisional Application No. 62/496,899 filed on Nov. 1, 2016, and U.S. Provisional Application No. 62/462,906 filed on Feb. 23, 2017. The content of each of the above referenced applications is incorporated by reference in its entirety.

TECHNICAL FIELD

The disclosure generally relates to medical devices, and more specifically to a system for reducing brain injury in an individual.

BACKGROUND

Sudden decelerating or accelerating head movements, which may be as a result of direct head impact in sports games (e.g., football), vehicular crashes, accidents (e.g., slips and falls), or on the battlefield, may produce immediate and/or progressive long term devastating brain injury. Such brain injury may be related to excessive brain movement inside of the calvarium which is associated with certain detrimental effects. Histological studies suggest that such injury may take place at the cellular level and adversely affects neuronal axons. As a result, locally damaging chemical and inflammatory responses may be set in motion. These pathophysiological events appear to be related to the sudden acceleration or deceleration of the head as well as the resulting momentum changes to the brain inside of the calvarium at these times.

Conventional efforts have been made to reduce head injury from forceful blows, specifically skull fractures, by means of helmets which have been designed to attenuate the transfer of external energy to the head from a collision. One example includes the design of rigid exterior helmets. Despite this effort brain injuries continue to occur. More recent helmet designs using flexible exterior, shock absorbing, multilayer helmets with novel flexible resilient interior baffles may offer better protection to the skull. However, these conventional approaches do not offer a means to limit brain motion inside of the skull, and as such, brain injury as a result of forceful blows to the head remains a concern.

SUMMARY

Embodiments of the invention include a brain injury reduction system that provides a protective measure to an individual that is currently experiencing or will undergo acceleration or deceleration of the head (e.g., resulting from impact or a blast pressure wave from an explosive device). A protective measure provided by the brain injury reduction system reduces an individual's brain movement relative to the calvarium during times of sudden decelerating or accelerating head movements, thereby reducing the severity of an injury that would be incurred by an individual's brain. Specifically, the brain injury reduction system reduces brain injury by decreasing venous drainage (e.g., maintaining or increasing a central venous pressure) from the brain at or immediately prior to the sudden head acceleration or deceleration. The reduced venous drainage corresponding to a maintained central venous pressure reduces the movement of the brain within the calvarium when a sudden deceleration or acceleration of the head occurs. This reduction in brain motion within the calvarium, in turn, results in less distortion or deformation of the brain tissues (straining or stretching of the tissues).

Generally, venous drainage from the intracranial compartment occurs via the jugular veins, and more specifically the internal jugular veins (IJV), when an individual is supine and the paravertebral venous plexus (PVP), also referred to as the vertebral venous plexus (VP) when upright. When an impact to the head (or blast pressure wave) occurs, increased venous drainage from the intracranial compartment may occur, thereby increasing the intracranial space within the head that allows the brain to displace within the calvarium. As such, a reduction in venous drainage from the intracranial compartment could reduce the intracranial space made available in the head and thereby reduce brain movement that is a consequence of the sudden acceleration or deceleration movement of the individual's head. Reduction of venous drainage through the PVP can be achieved by glottis closure (e.g., through a gag reflex) or through a valsalva maneuver (or through other mechanisms that reduce this venous drainage). Reduction of venous drainage through one or both of the IJV and external jugular veins (EJV) can be achieved through external compression of the IJV and EJV, respectively.

The brain injury reduction system decreases drainage of venous blood out of the intracranial compartment through one or both of the PVP and the IJVs at or immediately before the occurrence of a sudden acceleration or deceleration of an individual's head. Specifically, the brain injury reduction system includes components that may be worn by the individual such as a wearable head-impact and/or position-tracking sensing device (e.g., miniature sensors mounted into a helmet, mouthguard, or headband) as well as one or more wearable actuation devices that are each configured to reduce venous drainage through either the IJVs or PVP. For example, a wearable actuation device can be configured to reside around the neck of the individual and expand to externally compress the IJVs when required. As another example, a wearable actuation device can be configured to stimulate a gag reflex or a valsalva-like maneuver. Each of the devices are communicatively coupled with one another such that each of the one or more wearable actuation devices can instantaneously provide the protective measure in response to a detected event, such as an impending collision, by the wearable sensing device. The brain injury reduction system can subsequently terminate the protective measure after the occurrence of the collision or after a pre-determined endpoint occurs.

BRIEF DESCRIPTION OF THE DRAWINGS

The disclosed embodiments have advantages and features which will be more readily apparent from the detailed description, the appended claims, and the accompanying figures (or drawings). A brief introduction of the figures is below.

Figure 1A:
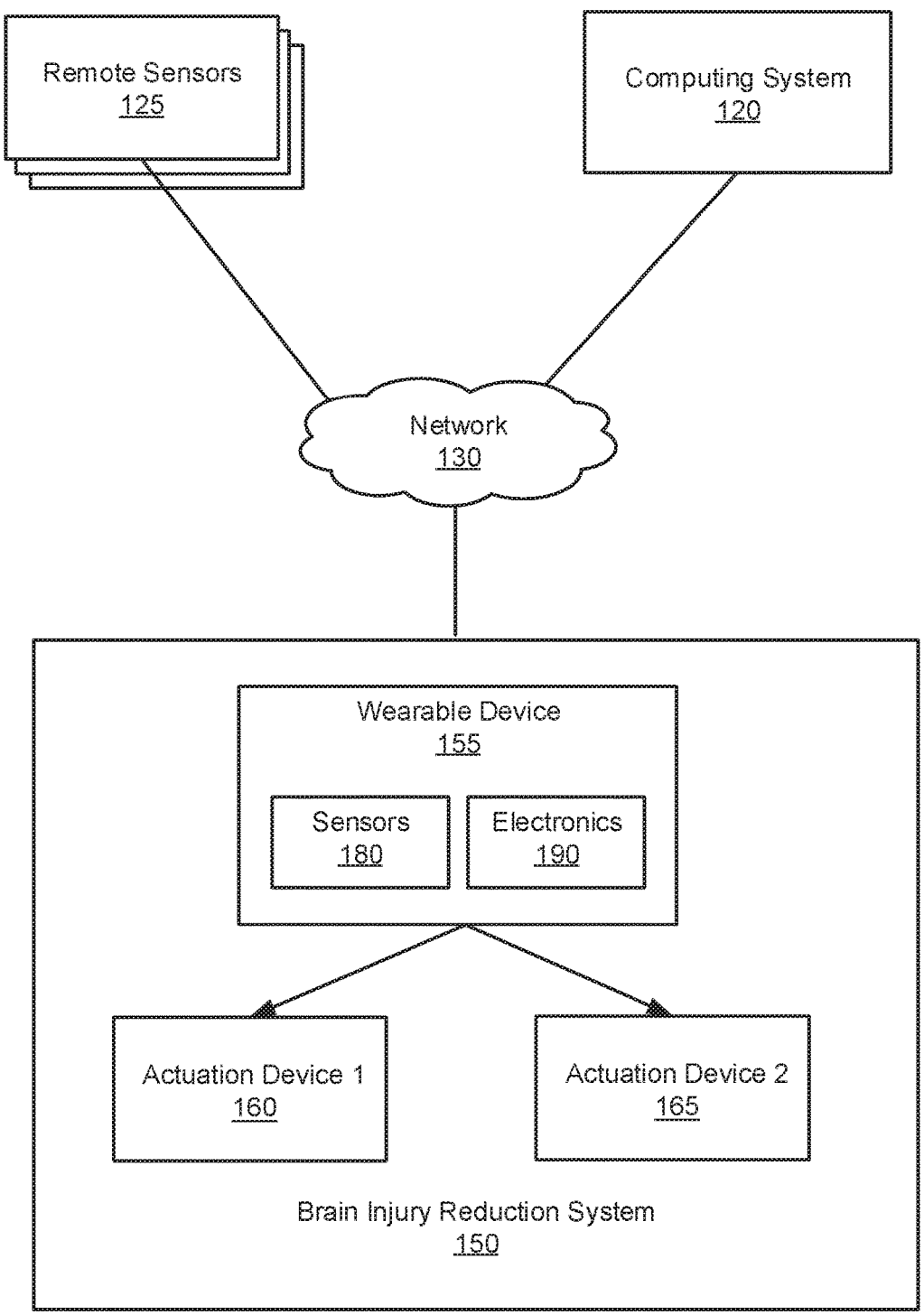
FIG. 1A illustrates an overall system environment for providing a protective measure for reducing brain injury in an individual, in accordance with an embodiment.

The Figures (FIGs.) and the following description relate to preferred embodiments by way of illustration only. It should be noted that from the following discussion, alternative embodiments of the structures and methods disclosed herein will be readily recognized as viable alternatives that may be employed without departing from the principles of what is claimed.

DETAILED DESCRIPTION

The FIGs. depict embodiments of the disclosed system (or method) for purposes of illustration only. One skilled in the art will readily recognize from the following description that alternative embodiments of the structures and methods illustrated herein may be employed without departing from the principles described herein.

Reference will now be made in detail to several embodiments, examples of which are illustrated in the accompanying figures. It is noted that wherever practicable similar or like reference numbers may be used in the figures and may indicate similar or like functionality. For example, a letter after a reference numeral, such as "320a," indicates that the text refers specifically to the element having that particular reference numeral. A reference numeral in the text without a following letter, such as "320," refers to any or all of the elements in the figures bearing that reference numeral (e.g. "actuating component 320" in the text refers to reference numerals "actuating component 320a" and/or "actuating component 320b" in the figures).

Overall System Environment

FIG. 1A illustrates an overall system environment 100 for providing a protective measure for reducing brain injury in an individual, in accordance with an embodiment. Generally, the overall system environment 10 includes a brain injury reduction system 150, a computing system 120, and remote sensors 125 that are interconnected through a network 130. As shown in FIG. 1A, the brain injury reduction system 150 may further include a wearable device 155, an actuation device 1 (160), and an actuation device 2 (165).

Although the illustrated environment 100 may include the elements shown in FIG. 1, in other embodiments the environment 100 may include different elements (e.g., additional or fewer elements). In one embodiment, the system environment 100 may include multiple brain injury reduction systems 150 in communication with one another, the computing system 120, and remote sensors 125 through the network 130. In some embodiments, the system environment 100 does not include a computing system 120 and/or the remote sensors 125. In various embodiments, the brain injury reduction system 150 includes one of the two actuation devices 160 or 165, or includes more than two actuation devices (e.g., three, four, or more actuation devices). In various embodiments, there are no sensors and/or electronics in the wearable device, and instead there are only one or more actuation devices that are actuated by some other mechanism (e.g., the remote sensors or computing system), or the actuation devices remain in an always on position such that an actuation signal is not needed. Furthermore, the functionalities of each element may be distributed differently among the elements in other embodiments.

Example Brain Injury Reduction System

As shown in FIG. 1A, a brain injury reduction system 150 includes a wearable device 155 as well as one or more actuation devices 160, 165. In various embodiments each of the wearable device 155 and actuation devices 160,165 are wearable and configured to be worn by a particular individual. As such, a brain injury reduction system 150 is responsible for reducing brain injury in a particular individual. In various embodiments, each of the wearable device 155, actuation device 1 (160), and actuation device 2 (160) includes wearable housings that contain components of each of the wearable device 155, actuation device 1 (160), and actuation device 2 (160).

Notably, the subsequent disclosure that describes each of the wearable device 155, actuation device 1 (160) and actuation device 2 (165) will refer to each device in one of a rest state or an actuated state. The rest state refers to the default state of each device when a protective measure is not provided. Each device can transition to an actuated state when a protective measure is needed. Specifically, when each device is in an actuated state, the brain injury reduction system 150 maintains the central venous pressure in the brain in the individual, thereby reducing brain injury due to decelerating or accelerating head motion (e.g., resulting from head impact or a pressure wave from an explosive device).

In one embodiment, the wearable device 155 is headwear, such as a helmet, worn by an individual. In other embodiments, the wearable device 155 can be worn on another anatomical location (e.g., chest, neck, hip, extremities such as arms or legs, and the like) of the individual. The wearable device 155 can be a wearable sensing device that includes sensors 180 and electronics 190. The sensors 180 of the wearable device 155 can be configured to detect an occurring or impending collision. The electronics 190 of the wearable device 155 may include one or more of a power source, processor, or communication hardware. Therefore, the electronics 190 of the wearable device 155 enable the wearable device 155 to communicate with the computing system 120 and/or remote sensors 125 through the network 130. Additionally, the electronics 190 of the wearable device 155 can enable the wearable device 155 to communicate with the actuation devices 160 and 165 (e.g., through Bluetooth, near field communication (NFC), WiFi, 2G, 3G, 4G, or long-term evolution (LTE)). Further description regarding the sensors 180 and electronics 190 of the wearable device 155 are described below in reference to FIG. 2.

Actuation device 1 (160) and an actuation device 2 (165) are each configured to stimulate and cause a type of an anatomical or physiological response in an individual that assists in the reduction of brain injury. In some embodiments, the brain injury reduction system 150 includes a single actuation device 160. In other embodiments, the brain injury reduction system 150 includes multiple actuation device 1 (160) that each causes or reinforces a first type of anatomical or physiological response in the individual and/or multiple actuation device 2 (165) that each causes a second type of anatomical or physiological response in the individual.

Figure 1B:
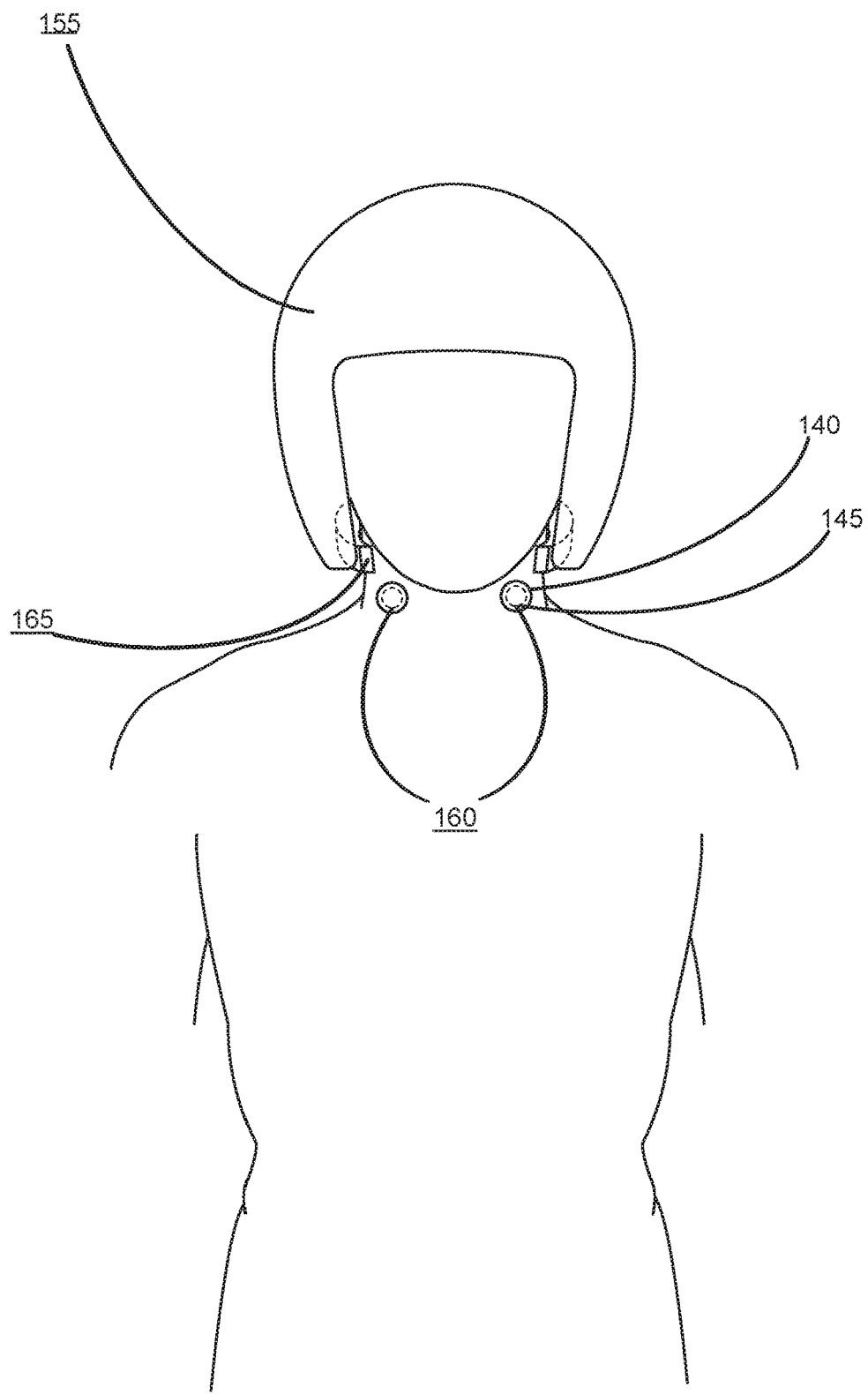
FIGS. 1B and 1C each illustrates components of the brain injury reduction system worn by an individual, in accordance with an embodiment.
Figure 1C:
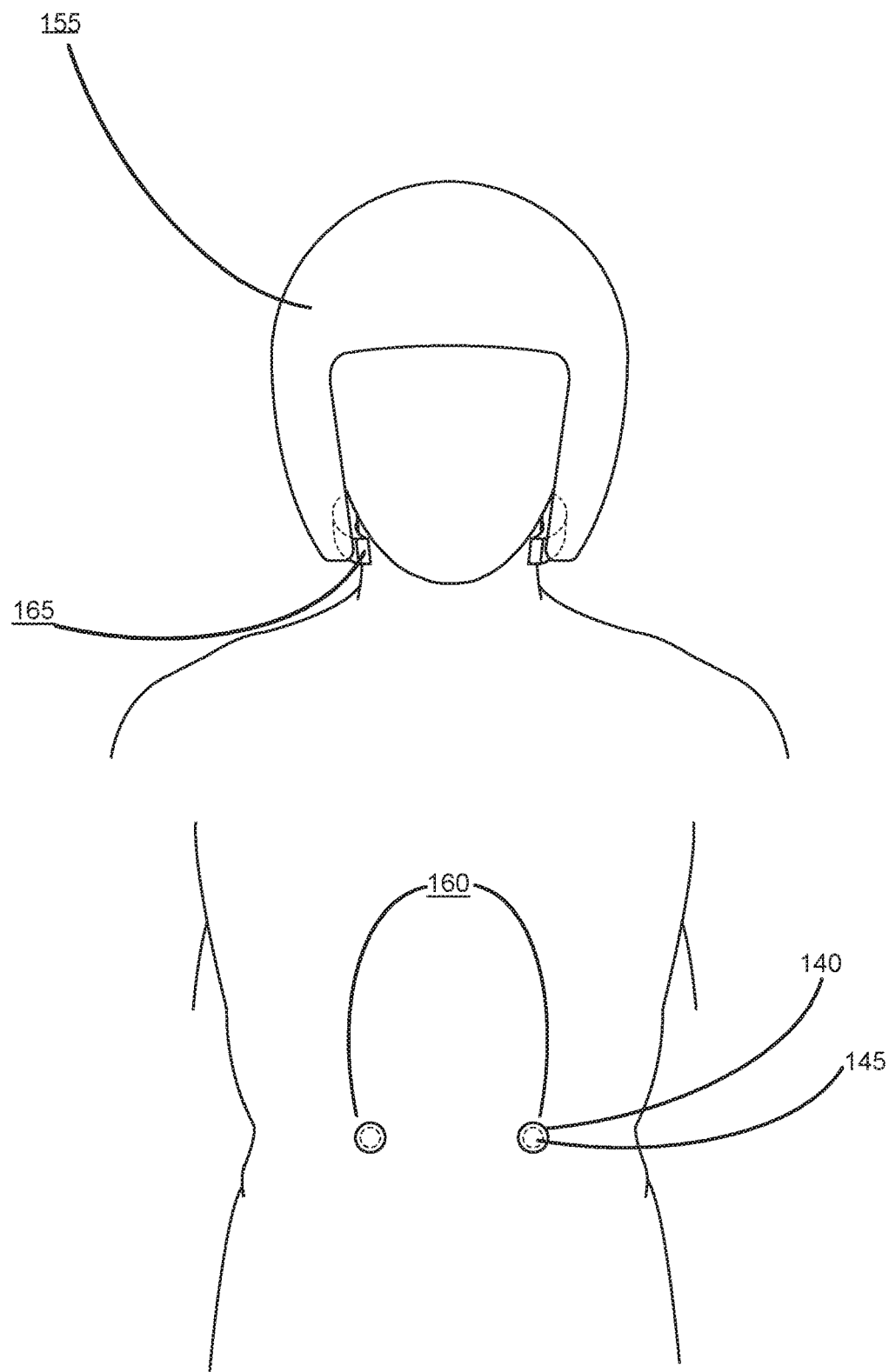

Reference is now made to FIG. 1B and FIG. 1C, which each illustrates components of the brain injury reduction system 150 worn by an individual, in accordance with an embodiment. Specifically, FIG. 1B depicts a wearable device 155 as a helmet, actuation device 1 (160), and actuation device 2 (165) that is configured to circumferentially surround a portion of the neck of the individual. In some embodiments, a wearable device 155 can be a wearable garment such as a shirt (e.g., football jersey), pants, shoes, protective wear (e.g., brace, pads), and the like.

Referring first to actuation device 2 (165) shown in FIG. 1B, the actuation device 2 (165) may be situated around the neck of the individual so as to be in close proximity to the skin of the individual under which the IJVs reside. In some embodiments, the actuation device 2 (165) is physically coupled to the wearable device 155 through one of straps, buckles, adhesives, buttons, and the like. In various embodiments the actuation device 2 (165) is removably coupled to wearable device 155. In other embodiments, the actuation device 2 (165) is a standalone device and separate from the wearable device 155.

When in an actuated state, actuation device 2 (165), may change its configuration to physically compress the IJVs, thereby reducing venous drainage through the IJV. For example, actuation device 2 (165) may include protrusions that extend from the housing of the actuation device 2 (165) to externally compress the IJVs. An example actuation device 2 (165) is described in further detail below in regards to FIG. 3.

Referring now to actuation device 1 (160), it is configured to cause one of a gag reflex or a valsalva-like maneuver in the individual when in an actuated state. Therefore, actuating the actuation device 1 (160) causes a reduction in venous drainage through the PVP. As depicted in FIG. 1B, actuation device 1 (160) can include a pair of stimulation structures such as electrode leads 145 in contact with the skin of the individual. These may be neuromuscular stimulation structures that are configured to stimulate a nerve and/or a muscle. Additionally, the electrode leads 145 may be located on or within an electrode housing 140. As an example, an electrode housing 140 may be an electrode pad that houses the electrode leads 145 such that the electrode housing 140 is in contact with the individual's skin.

In some embodiments, the electrode leads 145 or the electrode housing 140 is attached to the skin through any one of adhesives or gels. Such adhesives or gels can hold the electrode leads 145 or the electrode housing 140 in contact with the skin of the individual and, in some embodiments, can further improve the conductivity of the skin. In various embodiments, instead of a pair of electrode leads 145, a single electrode lead 145 in contact with the skin of the individual is sufficient to provide a stimulation. The electrode leads 145 may be connected (e.g., wired) to a power source such as a minimal battery such that the actuation device 1 (160) remains non-intrusive.

As depicted in FIG. 1B, the electrode leads 145 and the electrode housing 140 of the actuation device 1 (160) are spherical in shape. However, in other embodiments, the electrode leads 145 and electrode housing 140 may be square, rectangular, triangular, oval, hexagonal, or another polygon in shape. In various embodiments, the electrode leads 145 are between 1 millimeter and 10 millimeters in diameter. In other embodiments, the electrode leads 145 may be larger between 10 millimeters and 10 centimeters in diameter.

Each electrode lead 145 may be configured to provide a transcutaneous stimulation to a corresponding nerve located beneath the skin. Therefore, actuation of the electrode leads 145 (e.g., providing an electric input) can stimulate a nerve and result in a desired anatomic response. Specifically, actuation device 1 (160) depicted in FIG. 1B may contact the skin of the individual located external or near to the laryngeal nerves and therefore causes a glottic closure as a result of stimulating the laryngeal nerves.

Referring now to FIG. 1C, the actuation device 1 (160) may be placed in contact with the skin of the individual at a different anatomical location. Specifically, as shown in FIG. 1C, actuation device 1 (160) may include stimulation structures such as electrode leads 145 that are in contact with the skin of the individual located above or near the thoraco-abdominal nerves. Also depicted in FIG. 1C are electrode housings 145 that are configured to house the electrode leads 140. In this scenario, actuation of the actuation device 1 (160) causes a valsalva-like maneuver as a result of stimulating the thoraco-abdominal nerves or the rectus abdominal muscles directly.

Although FIG. 1B and FIG. 1C each depict two different embodiments of actuation device 1 (160), in various embodiments, the actuation device 1 (160) may include a first set of electrode leads 145 in contact with the skin of the individual that is configured to stimulate the laryngeal nerves as well as a second set of electrode leads 145 in contact with the skin of the individual that is configured to stimulate the thoraco-abdominal nerves. As such, actuation of actuation device 1 (160) can cause both a gag reflex and a valsalva-like maneuver.

The actuation device 1 (160) and the actuation device 2 (165) may each contain electronics that enable each actuation device 160 and 165 to communicate with the wearable helmet 155. More specifically, the actuation device 1 (160) and the actuation device 2 (165) can receive input from the wearable helmet 155 through the electronics that cause each actuation device 160 and 165 to actuate. Altogether, actuation of one or both of actuation device 1 (160) and actuation device 2 (165) maintains or increases the venous pressure within the individual's brain due to a reduction in venous drainage. Additional embodiments of actuation devices 160 and 165 are described in further detail below in regards to FIGS. 2-5.

Example Remote Sensors

Referring back to FIG. 1, the system environment may include remote sensors 125 that can be a data gathering sensor. For example, a remote sensor 125 may be a sensor capable of capturing signals including, but not limited to, electromagnetic radiation and acoustic signals. For example, a remote sensor 125 may be a camera with a charge coupled device that captures an image by capturing individual pixels of light intensities. As another example, a remote sensor 125 may be in an aerial vehicle (e.g., a drone) that can capture signals.

In one embodiment, the remote sensors 125 may gather data in relation to the wearable device 155 of the brain injury reduction system 150. More specifically, the remote sensors 125 gather the position and orientation of the wearable device 155 prior, during, and subsequent to a collision which may cause head impact. Additionally, the remote sensors 125 gathers data corresponding to the collision which can include the speed of collision and estimated overall force imparted due to collision.

In various embodiments, the remote sensors 125 can gather data corresponding to multiple brain injury reduction systems 150. As a specific example, if the system environment 100 is employed for a football game, a first brain injury reduction system 150 can be associated with a first player and a second brain injury reduction system 150 can be associated with a second player. Therefore, the remote sensors 125 can track data corresponding to a collision between the first player and the second player. As an additional example, the remote sensors 125 can track the positions and/or speeds of the first player and the second player and detect an impending collision given their tracked positions and/or speeds.

In various embodiments, the remote sensors 125 can be in communication with the computing system 120. Therefore, the remote sensors 125 provide the gathered data corresponding to a wearable device 155 or the gathered data corresponding to a collision to the computing system 120 for analysis.

Example Computing System

A computing system 120 is in communication with the remote sensors 125 and one or more brain injury reduction systems 150 through the network 130. A computing system 120 may be a server computer, a client computer, a personal computer (PC), a tablet PC, a set-top box (STB), a smartphone, an internet of things (IoT) appliance, a network router, switch or bridge, or any machine capable of executing instructions (e.g., program code or software) stored in a memory that specify actions to be taken by that computing system 120.

In various embodiments, the computing system 120 receives data captured by one or both of the remote sensors 125 and data captured by the brain injury reduction system 150. The computing system 120 analyzes the data to improve upon the response to future collisions. As an example, the computing system 120 can more accurately determine whether a protective measure is needed. In some scenarios, a protective measure is needed when an individual is currently experiencing or will experience a collision that is unexpected. Alternatively, a protective measure is unneeded when an individual has anticipated an occurring collision or is anticipating for an impending collision.

In one embodiment, when a subsequent occurring or impending collision is detected, the computing system 120 receives data corresponding to that occurring or impending collision and determines whether a protective measure is needed. In other embodiments, the computing system 120 provides analysis information to the wearable device 155 such that when a subsequent occurring or impending collision is detected, the wearable device 155 can perform the analysis to determine whether a protective measure is needed. Further discussion regarding the computing system 120 is described below in reference to FIG. 6.

Example Network

The network 130, which can be wired, wireless, or a combination thereof, enables communications between the brain injury reduction system 150, the computing system 120, and the remote sensors 125. The network 130 may include the Internet, a local area network (LAN), virtual LAN (VLAN) (e.g., with VPN), wide area network (WAN), or other network. In one embodiment, the network 130 uses standard communications technologies and/or protocols, such as Hypertext Transfer Protocol (HTTP), Transmission Control Protocol/Internet Protocol (TCP/IP), Uniform Resource Locators (URLs), and the Doman Name System (DNS). In another embodiment, the brain injury reduction system 150, the computing system 120, and the remote sensors 125 can use custom and/or dedicated data communications technologies instead of, or in addition to, the ones described above.

Example Wearable Device

Figure 2:
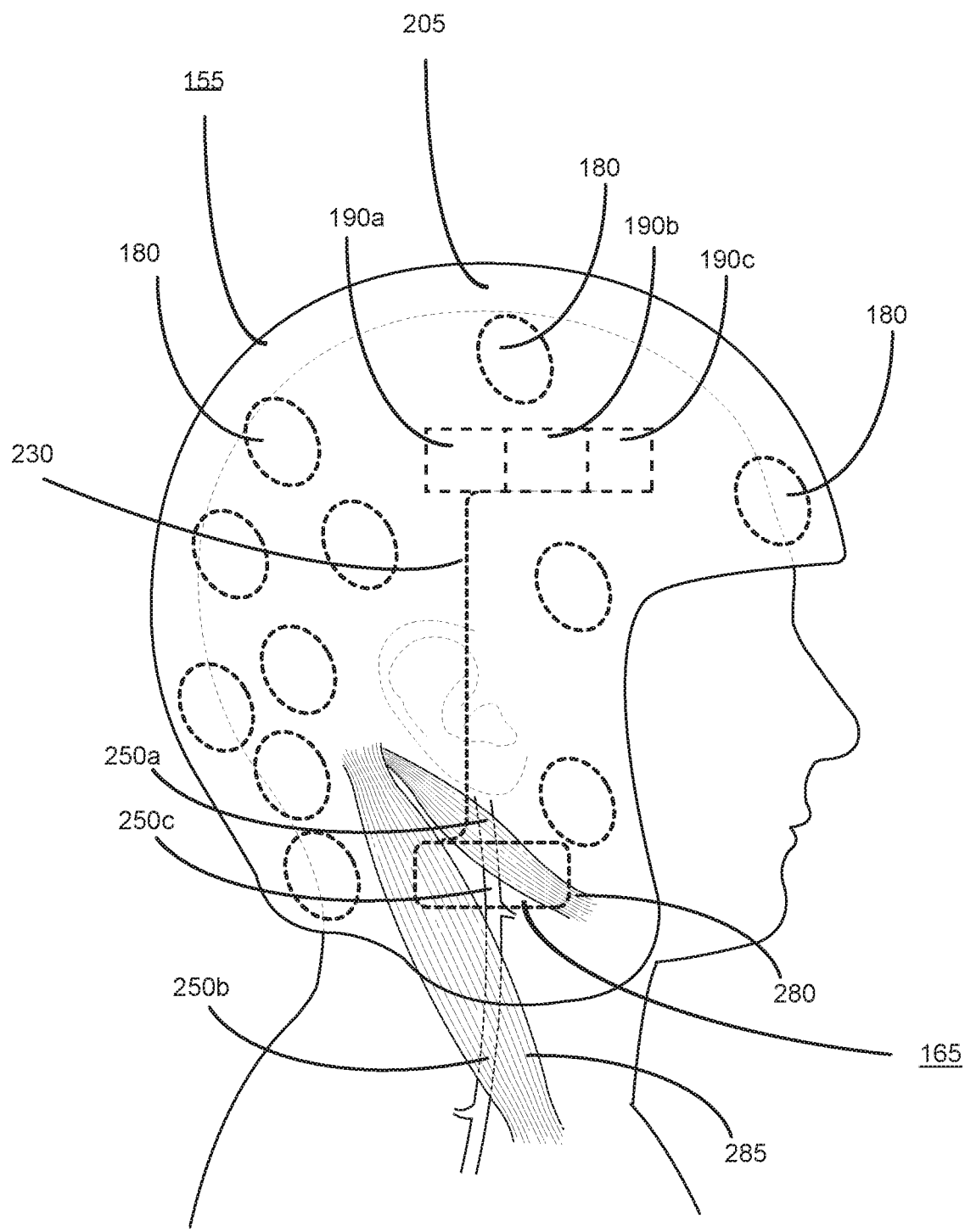
FIG. 2 illustrates a right side view of a wearable device in communication with an actuation device, in accordance with an embodiment.

FIG. 2 illustrates a right side view of a wearable device 155 in communication with an actuation device 2 (165), in accordance with an embodiment. The wearable device 155 can include sensors 180 and electronics 190. In some embodiments, the wearable device 155 includes wired connections 230 that enable the electronics 190 of the wearable device 155 to communicate with the actuation device 2 (165).

Referring to the sensors 180 of the wearable device 155, FIG. 2 depicts multiple sensors 180 distributed throughout the wearable device 155. In some embodiments, the sensors 180 are housed on or within a wearable housing 205 of the wearable device 155. For example, the wearable housing 205 may be the rigid helmet itself or a component within the rigid helmet. In various embodiments, the sensors 180 are evenly distributed or within the wearable housing 205 of the wearable device 155. In other embodiments, the concentration of sensors 180 at a location on or within the housing 205 of the wearable device 155 may be different where the individual may be more susceptible to brain injury. For example, as depicted in FIG. 2, the posterior of the wearable device 155 may include a higher concentration of sensors 180 in order to more accurately detect an occurring or impending collision that may be approaching from the posterior of a vulnerable individual.

The sensors 180 may be circular in shape. However, in various embodiments, the sensors 180 may be square, rectangular, triangular, oval, hexangular, or another polygon in shape. In some embodiments, the size of each sensor 180 can range from 1 millimeter to 5 centimeters or more in both size and thickness. In other embodiments, the size of the sensor 180 is larger and maintains its function of capturing a signal.

In one embodiment, the sensors 180 may be located on the external surface of the housing of the wearable device 155. In this scenario, the sensors 180 may be pressure sensors configured to detect changes in acoustics (e.g., pressure waves) in the vicinity of the sensors 180. As another example, the sensors 180 may be electromagnetic sensors configured to detect changes in electromagnetic radiation (e.g., energy across the electromagnetic spectrum such as light or magnetic waves) in the vicinity of the sensors 180. Generally, the changes in acoustics and/or changes in electromagnetic radiation may arise from an approaching object. Therefore, the sensors 180 on the external surface of the wearable device 155 can detect an impending collision due to the approaching object. In various embodiments, the sensors 180 detect an impending collision between 0 to 1 seconds beforehand. In some embodiments, the sensors 180 detect an impending collision between 100 to 500 milliseconds beforehand. In various embodiments, the sensors 180 detect an impending collision between 200 and 300 milliseconds beforehand.

In some embodiments, the sensors 180 may be located on an internal surface (e.g., on an inner most surface or within two layers) of the housing 205 of the wearable device 155. In this scenario, the sensors 180 may be one or both of accelerometers or gyroscopes that are configured to gather data regarding the orientation and/or position of the wearable device 155. An accelerometer can gather the linear kinematics (e.g., acceleration and velocity) along one or more axes of the wearable device 155 whereas the gyroscope can gather the rotational kinematics (e.g., acceleration and velocity) along one or more rotational axes of the wearable device 155.

In various embodiments, a wearable device 155 can include sensors 180 located on both the external surface and the internal surface of the wearable device 155. For example, the wearable device 155 can include sensors 180 (e.g., pressure or electromagnetic sensors) configured to detect an impending collision from an approaching object as well as sensors 180 (e.g., accelerometer and gyroscope) configured to detect the orientation and/or position of the wearable device 155.

Referring now to the electronics 190 of the wearable device 155, the electronics 190 may include one or more of communication electronics 190a (e.g., that enable communication via Bluetooth, NFC, WiFi, 2G, 3G, 4G, or LTE), processor 190b, and power source 190c (e.g., battery). In various embodiments, the communication electronics 190a, the processor 190b, and power source 190c can be distributed at different locations around the wearable device 155. Each of the communication electronics 190a, processor 190b, and power source 190c can be housed within the housing 205 of the wearable device 155. Generally, the power source 190c provides power to the sensors 180, communication electronics 190a, and processor 190b of the wearable device 155.

Specifically, the communication electronics 190a enable the wearable device 155 to communicate with the remote sensors 125 and the computing system 120 through the network 130. Additionally, the communication electronics 190a enable the wearable device 155 to communicate with the actuation device 1 (160) and the actuation device 2 (165).

In one embodiment, the communication electronics 190a of the wearable device 155 receives a trained machine-learning model to be applied by the processor 190b to determine whether a protective measure is required. In another embodiment, the communication electronics 190a of the wearable device 155 receives instructions from the computing system 120 indicating that a protective measure is required. Thus, the communication electronics 190a of the wearable device 155 can provide an input to one or both of the actuation device 1 (160) and the actuation device 2 (165) to transition from a rest state to an actuated state in order to reduce venous drainage from the individual's head. Additionally, the communication electronics 190a of the wearable device 155 can provide an input to one or both of the actuation device 1 (160) and the actuation device 2 (165) to cease actuation and transition back into a rest state.

In some embodiments, the wearable helmet 155 includes wired connections 230 such that the communication electronics 190a can directly communicate with actuation device 2 (165) through the wired connection 230. A wired connection 230 may be preferable to reduce the latency as compared to wireless communication methods.

Referring now to the processor 190b of the wearable helmet 155, in various embodiments, the processor 190b can be configured to execute instructions (e.g., code) that determine whether a protective measure is needed. Therefore, in this scenario, the processor 190b of the wearable helmet 155 receives a trained machine-learning model from the computing system 120 to be used to determine whether a protective measure is needed. For example, the processor 190b of the wearable helmet 155 can receive sensor-gathered data from the sensors 180 of the wearable helmet 155 and apply the sensor-gathered data as input to the trained machine-learning model. More specifically, the trained machine-learning model analyzes the sensor data (e.g., orientation and/or position of the wearable helmet 155 and/or impending collision information) and outputs whether the protective measure is to be performed. As an example, the machine-learning model may be trained to classify impending collisions that a vulnerable individual is not expecting (e.g., from the posterior of the individual) as requiring a protective measure. Therefore, if a protective measure is deemed necessary by the machine learning model, the processor 190b instructs the communication electronics 190a to transmit inputs to actuate one or both of actuation device 1 (160) and actuation device 2 (165).

In various embodiments, the processor 190b further detects an endpoint and subsequently instructs the communication electronics 190a to provide an input to one or both of actuation device 1 (160) and actuation device 2 (165) to transition from an actuated state back to the rest state. Therefore, the individual that was provided the protective measure need not experience prolonged physical compression on the IJV and/or a prolonged induced gag reflex and/or valsalva-like maneuver.

In various embodiments, the detected endpoint may be a collision. For example, a preventive measure can initially be provided in response to an impending collision. Once the impending collision occurs, the processor 190b detects the occurred collision as an endpoint and provides input such that the actuation device 1 (160) and/or actuation device 2 (165) transitions back to the rest state. In some embodiments, the endpoint is the detection of multiple collisions. For example, a first collision may correspond to a collision with a moving object (e.g., a collision with another football player) whereas a second collision may correspond to a collision with an inanimate object (e.g., the ground). Therefore, the protective measure may be held and provided through the multiple collisions. Once the processor 190b receives notification that multiple collisions were detected, the processor 190b can provide input to transition the actuation device 1 (160) and/or actuation device 2 (165) back to the rest state. In some embodiments, the detected endpoint is a threshold duration of time. For example, the duration may be several seconds (e.g., 3 seconds, 5 seconds, or 10 seconds). After the threshold duration of time has passed, the processor 190b causes the actuation device 1 (160) and/or actuation device 2 (165) to transition back to the rest state.

Example Actuation Device for Closing Internal Jugular Veins

Referring to FIG. 2, the actuation device 2 (165) may be located on the interior of the housing 205 wearable device 155. Specifically, the actuation device 2 (165) is located between the wearable device 155 and the skin of the individual that is external to the jugular veins. In some embodiments, the actuation device 2 (165) is configured to compress one or both of the left/right internal jugular veins (IJV) and the external jugular veins (EJV). Although FIG. 2 depicts a right side view of the actuation device 2 (165) that is configured to externally compress the one or both of the right IJV and right EJV, one skilled in the art can readily understand that the actuation device 2 (165) can be configured to provide bilateral compression to both the right and left IJV/EJV. Therefore, the subsequent description refers to both the right and left IJV/EJV.

FIG. 2 further depicts the anatomical structure of the right IJV of the human individual. Specifically, the digastric muscle 280 is positioned superficially relative to a first portion 250a of the IJV. In other words, the digastric muscle 280 covers and prevents external access through the skin to the first portion 250a of the IJV. Additionally, the sternocleidomastoid muscle 285 is positioned superficially relative to a second portion 250b of the IJV. In other words, the sternocleidomastoid muscle 285 covers and prevents external access through the skin to the second portion 250b of the IJV. As shown in FIG. 2, the first portion 250a of the IJV is proximal to the individual's brain relative to the second portion 250b of the IJV. A third portion 250c of the IJV is externally accessible by compression through the skin. Therefore, the actuation device 2 (165) can be in contact with the skin of the individual located external to the third portion 250c of the IJV such that the actuation device 2 (165), when actuated, physically compresses and reduces venous drainage through the IJV.

Figure 3A:
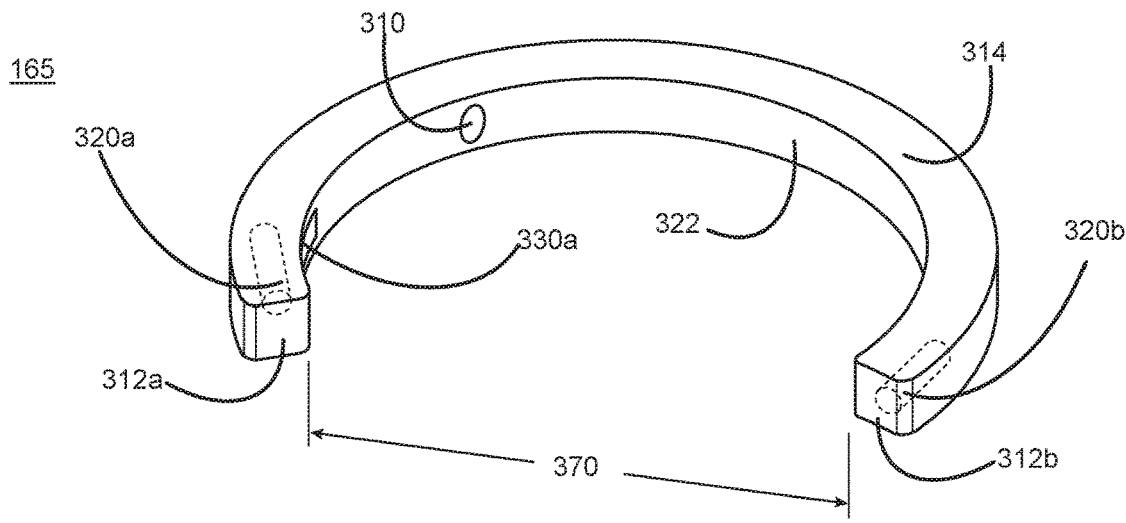
FIGS. 3A-C illustrates an example actuation device for compressing the jugular veins of an individual, in accordance with an embodiment.
Figure 3B:
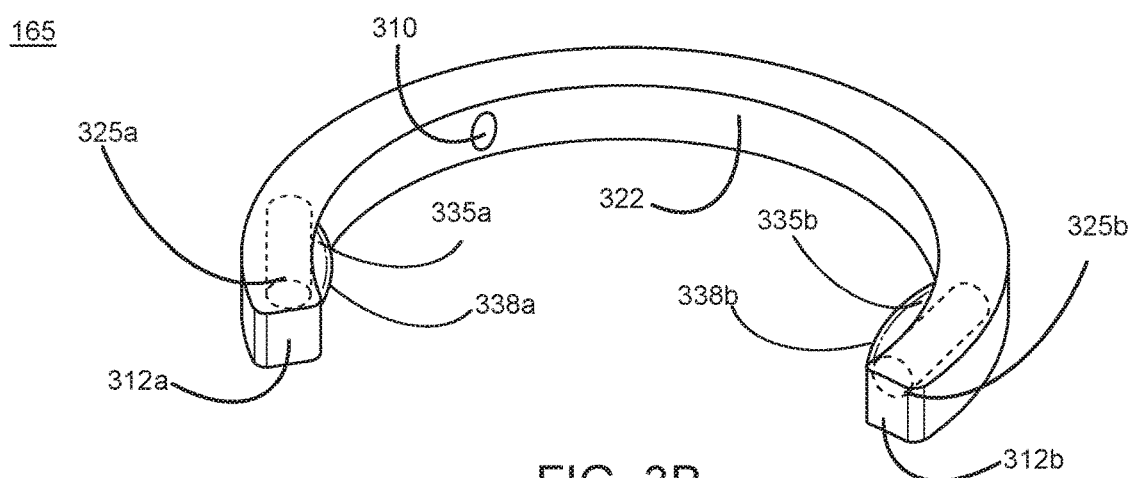
Figure 3C:
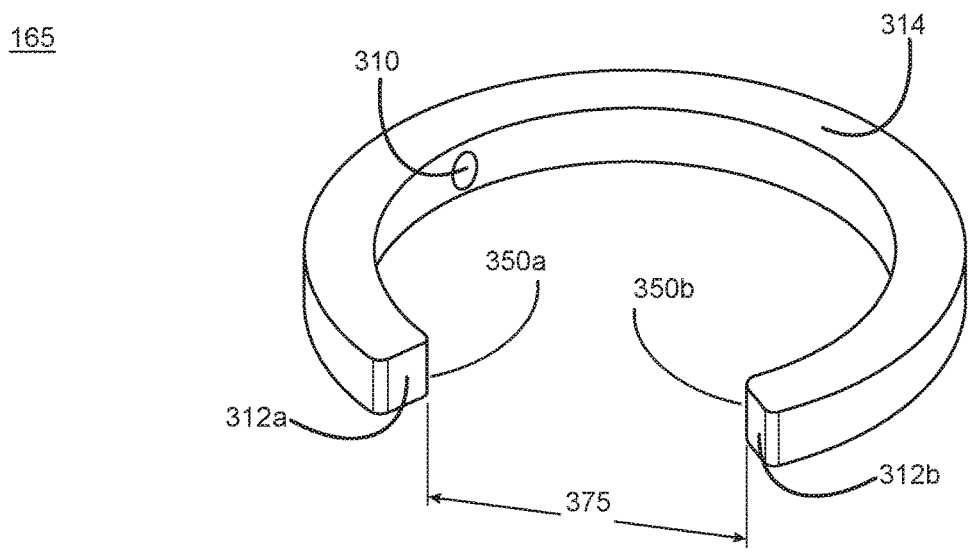

Reference is now made to FIGS. 3A-3C, which each illustrates an example actuation device 2 (165) for compressing the IJVs of an individual, in accordance with an embodiment. More specifically, FIG. 3A depicts the actuation device 2 (165) in a rest state. The actuation device 2 (165) may be composed of a body, otherwise referred to as the housing 314. The housing 314 may include a first end 312a and a second end 312b. The actuation device 2 (165) includes communication electronics 310 that enable the actuation device 2 (165) to communicate with the wearable device 155 through one of Bluetooth, near field communication (NFC), WiFi, 2G, 3G, 4G, LTE, or other wireless or wired communication methods. In some embodiments, the actuation device 2 (165) further includes stimulation structures. In FIG. 3A, these stimulation structures include an extendable structure 330a located on an inner surface 322 of the housing 314 of the actuation device 2 (165) near the first end 312a. Of note, the actuation device 2 (165) may also include an extendable structure located on an inner surface 322 of the housing 314 of the actuation device 2 (165) near the second end 312b which is not shown in FIG. 3A. Additionally, the actuation device 2 (165) can include one or more actuating components 320.

Referring first to the communication electronics 310 of the actuation device 2 (165), they enable the actuation device 2 (165) to communicate with the wearable device 155. Specifically, the communication electronics 310 of the actuation device 2 (165) receives input from the wearable device 155 after a protective measure is deemed necessary. Therefore, the actuation device 2 (165) can transition from a rest state, as depicted in FIG. 3A, to an actuated state as is depicted in FIGS. 3B and 3C. Alternatively, the communication electronics 310 can receive input from the wearable device 155 after an endpoint is detected. Therefore, the actuation device 2 (165) can transition from the actuated state back to the rest state. Although FIG. 3A depicts the communication electronics 310 as being located on the inner surface 322 of the housing 314 of the actuation device 2 (165), in various embodiments, the communication electronics 310 can be located on another surface of the housing 314 or internally within the housing 314 of the actuation device 2 (165).

In various embodiments, the housing 314 and the extendable structures 330 of the actuation device 2 (165) are each constructed from a solid polymer including, but not limited to, polystyrene, polypropylene, polyurethane, nylon, leather, rubber, and the like. Therefore, any component of the actuation device 2 (165), and more specifically the extendable protrusions 330, that contact the individual would retain its structure, thereby enabling the actuation device 2 (165) to physically compress the IJVs.

The actuation device 2 (165) may have dimensional characteristics that are tailored for the individual that wears the actuation device 2 (165). Specifically, the first end 312a and the second end 312b of the actuation device 2 (165) may be a pre-determined distance 370 apart. The pre-determined distance 370 can be selected according to the anatomical characteristics of the individual (e.g., neck size of the individual). Additionally, the housing 314 of the actuation device 2 (165) may have a curvature that is also selected according to the anatomical characteristics of the individual. For example, the curvature of the housing 314 can be designed to allow for about a 1 centimeter gap between actuation device 2 (165) and the neck of the individual when the actuation device 2 (165) is in a rest position. In other embodiments, the curvature of the housing 314 is designed to allow for a gap anywhere from 0.1 mm to 100 mm between actuation device 2 (165) and the neck of the individual when the actuation device 2 (165) is in a rest position. As such, the actuation device 2 (165) need not contact the skin of the individual in the rest position until a protective measure is determined to be required, which can trigger the actuation device 2 (165) to transition into the actuated state. Generally, the pre-determined distance 370 and the curvature of the housing 314 are selected such that the internal surface 322 of the actuation device 2 (165) remains a distance away from the skin of the individual when the actuation device 2 (165) is in the rest state. In some embodiments the internal surface 322 of the actuation device (165) may rest on the skin of the individual.

As described above, the housing 314 of the actuation device 2 (165) may include a first extendable protrusion 330a and a second extendable protrusion 330b on an internal surface 322 of the actuation device 2 (165). Additionally, the housing 314 of the actuation device 2 (165) can further house multiple actuating components 320. In some embodiments, each actuating component 320 is located within the actuation device 2 (165) as is indicated by the dotted outline structure in FIG. 3A. In various embodiments, the housing 314 may only include a single actuating component 320 that is configured to trigger both extendable protrusions 330a and 330b.

In the rest state, each extendable protrusion 330 can sit flush with the internal surface of the actuation device 2 (165). Therefore, in the rest state, each extendable protrusion 330 is unlikely to unintentionally contact the individual's skin and the underlying IJV. Each extendable protrusion 330 can transition from a rest state (e.g., flush to the inner surface 322) to an actuated state (e.g., extended outward from the inner surface 322) due to actuating components 320 of the actuation device 2 (165).

Each actuating component 320 of the actuation device 2 (165) can be triggered when the communication electronics 310 of the actuation device 2 (165) receives the input indicating a need for a protective measure from the wearable device 155. As shown in FIG. 3A, the actuation device 2 (165) includes two actuating components 320. A first actuating component 320a can be located within the housing 314 near or at the first end 312a whereas the second actuating component 320b can be located within the housing 314 near or at the second end 312b.

An actuating component 320 can provide one of a mechanical, chemical, or electrical inputs to cause an extendable protrusion 330 to change its configuration. This may occur in response to the communication electronics 310 receiving an input from the wearable device 155. For example, the actuating component 320 may be a physical structure that displaces inward. As such, the actuating component 320 mechanically displaces the extendable protrusion 330 to protrude inward from the inner surface 322. As another example, the actuating component 320 may store expandable fluids in separate compartments or cartridges such as gasses, liquids, gels, and the like. Thus, the expandable fluids can be mixed when desired that causes an increase in volume. The increase in volume can cause the extendable protrusions 330 to change their configuration and protrude inward from the inner surface 322. As another example, the actuating component 320 may include electrical components that provide an electrical input that cause the extendable protrusions 330 to change their configuration.

FIG. 3B depicts one embodiment of the actuation device 2 (165) in an actuated state. Specifically, each actuating component 325a and 325b may now be in an actuated state, as indicated by their larger size in FIG. 3B as compared to their counterparts 320a and 320b shown in FIG. 3A. Each actuated actuating component 325 causes a corresponding change to achieve an extended protrusion 335a and 335b. For example, each extended protrusion 335 is extended inward from the inner surface 322 when in an actuated state. Therefore, the first extended protrusion 335a can physically compress the right EJV and/or IJV whereas the second extended protrusion 335b can physically compress the left EJV and/or IJV. In some embodiments, the actuation device 2 (165) can have two extended protrusions 335 on either side (total of four extended protrusions 335), each extended protrusion configured to physically compress one of the right EJV, right IJV, left EJV, and left IJV.

As shown in FIG. 3B, each extended protrusion 335 may possess a convex rounded edge 338 that extends inward from the inner surface 322. As such, the rounded edge 338 of the extended protrusion 335 physically compresses the EJV and/or IJV of the individual. In other embodiments, the extended protrusion 335 may have other configurations such as a square, rectangular, or other polygonal shapes that may enable the extended protrusion 335 to focally compress the EJV and/or IJV of the individual.

In various embodiments, when the actuation device 2 (165) is in the actuated state, the distance between the first end 312a and the second end 312b remains unchanged in comparison to the distance when the actuation device 2 (165) is in the rest state. In some embodiments, as is shown in FIG. 3C, the distance 375 between the first end 312a and the second end 312b decreases when the actuation device 2 (165) transitions to the actuated state.

In this embodiment, the housing 314 may be composed of a flexible material. As such, when transitioning from the rest state to the actuated state, the housing 314 of the actuation device 2 (165) can reduce its curvature such that the reduced distance 375 between the first end 312a and the second end 312b is decreased compared to the distance 370 shown in FIG. 3A. In some embodiments, the flexible material is an electroactive polymer such as a liquid crystalline polymer, or a piezoelectric polymer.

As shown in FIG. 3C, the actuation device 2 (165) need not include extendable protrusions 330 as was shown in FIGS. 3A and 3B. In various embodiments, the first end 312a and the second end 312b each have vertical edges 350a and 350b, respectively. The vertical edges 350 of each the first end 312a and second end 312b can physically contact the skin of the individual, thereby bilaterally compressing the IJV of the individual.

Example Actuation Device for Closing the Paravertebral Venous Plexus

Example Device for Stimulating a Gag Reflex

Figure 4A:
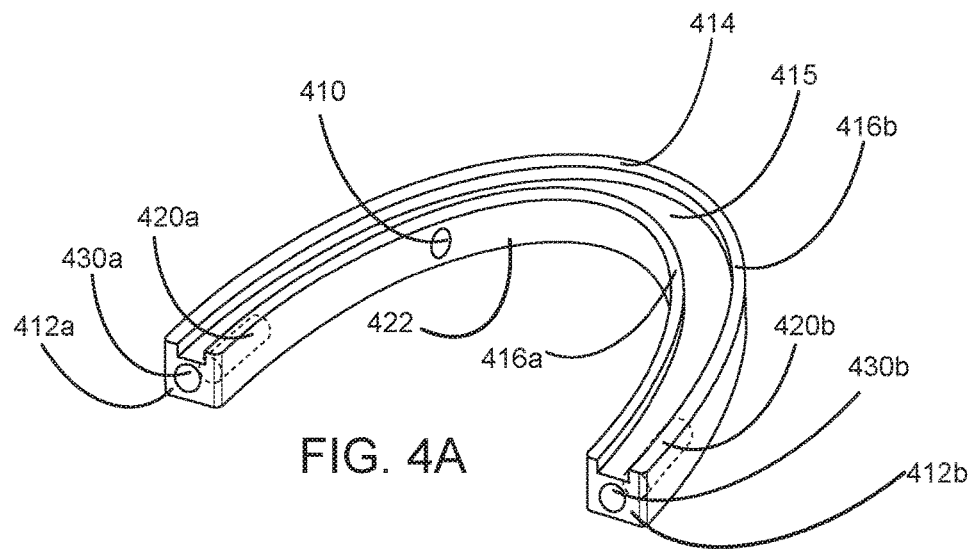
FIGS. 4A-4C each illustrates an example actuation device for inducing a gag reflex in an individual, in accordance with an embodiment.
Figure 4B:
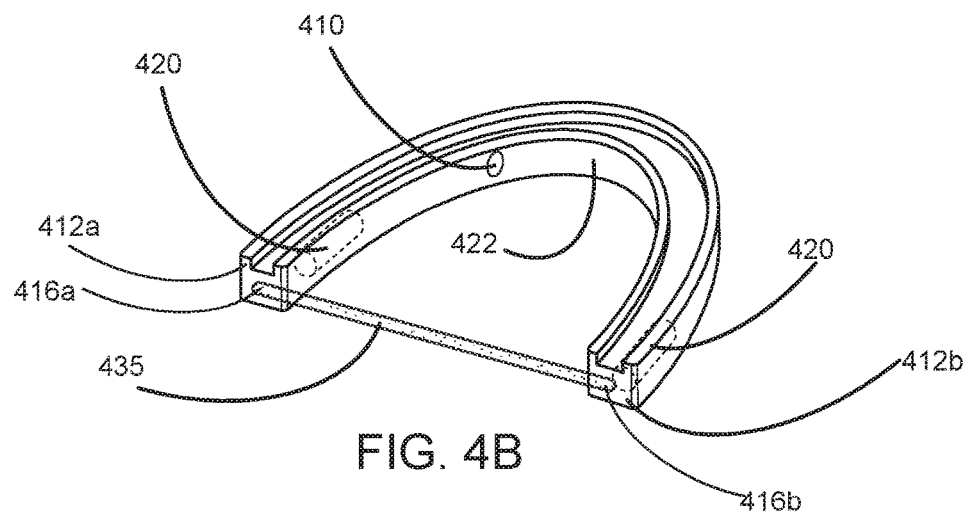
Figure 4C:
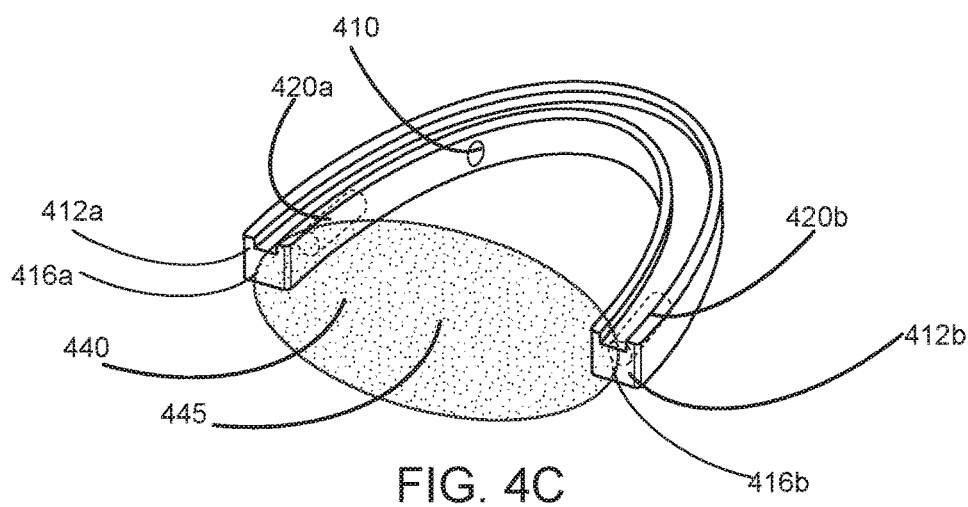

FIGS. 4A-C each illustrates an example actuation device 160 for inducing a gag reflex in an individual, in accordance with an embodiment. In one embodiment, a gag reflex can be invoked by the actuation device 1 (160) by physically contacting the actuation device 1 (160) with one or more various locations within the individual's mouth. For example, the stimulation structures of the actuation device 1 (160) may contact the back of the tongue, at or around the tonsils, the uvula, or the back of the throat. The physical contact can result in stimulation of the glossopharyngeal nerve, thereby resulting in a gag reflex. In other embodiments, a gag reflex can be invoked by the actuation device 1 (160) by directly electrically stimulating a nerve, such as the glossopharyngeal nerve, to cause the gag reflex.

Specifically, FIG. 4A depicts the actuation device 1 (160) in a rest state. The actuation device 1 (160) may be configured to be worn in a mouth of the individual. For example, as depicted in FIG. 4A, the actuation device 1 (160), is designed as a mouthguard device configured to reside within the mouth of the individual. Specifically, the actuation device 1 (160) may include a housing 414 that further includes a first end 412a and a second end 412b. The housing 414 may be contoured (e.g. curved) and may include features such as an inner ridge 416a, and outer ridge 416b, and a cavity 415 formed by the inner ridge 416a and outer ridge 416b. Additionally, the actuation device 1 (160) can include communication electronics 410, actuating components 420, and stimulation structures 430.

Referring first to the housing 414 of the actuation device 1 (160), as depicted in FIG. 4A, the housing 414 includes the inner ridge 416a and the outer ridge 416b. The inner ridge 416a forms the internal surface 422 of the actuation device 1 (160) and connects the first end 412a of the housing 414 to the second end 412b of the housing 414. The outer ridge 416b forms an external surface of the actuation device 1 (160) and similarly connects the first end 412a of the housing 414 to the second end 412b of the housing 414. A cavity 415 can be located between the inner ridge 416a and the outer ridge 416b. In other words, the cavity 415 is lined on either side by one of the inner ridge 416a or the outer ridge 416b. In some embodiments, the cavity 415 has a depth between 1 millimeter and 20 millimeters. Specifically, the depth of the cavity 415 can be designed such that the individual's teeth can comfortably reside in the cavity 415 when the actuation device 1 (160) is worn in the mouth. Furthermore, the cavity 415 (as well as the inner ridge 416a and outer ridge 416b) is shaped with a particular curvature. In various embodiments, the curvature may be determined based on the curvature of the individual's teeth.

As depicted in FIG. 4A, the cavity 415 is located on a top side of the actuation device 1 (160) and therefore, enables an individual's upper teeth to rest comfortably in the cavity 415 when the actuation device 1 (160) is worn. In various embodiments, the actuation device 1 (160) further includes a cavity (not shown) on the underside of the actuation device 1 (160). The cavity on the underside of the actuation device 1 (160) may be similarly configured as the cavity 415 on the top side of the actuation device 1 (160). As such, the cavity on the underside of the actuation device 1 (160) may similarly enable an individual's lower teeth to rest comfortably in the cavity when wearing the actuation device 1 (160). In some embodiments, the cavity 415 on either the top or underside of the actuation device 1 (160) includes additional features such as undulations or indentations that are designed to mimic the shape (e.g., gaps, indentations and the like) of the individual's upper or lower teeth.

Referring to the communication electronics 410 of the actuation device 1 (160), they enable the actuation device 1 (160) to communicate with the wearable device 155 through one of Bluetooth, near field communication (NFC), WiFi, 2G, 3G, 4G, LTE, or other wireless or wired communication methods. Specifically, the communication electronics 410 of the actuation device 1 (160) receives input from the wearable device 155 after a protective measure is deemed necessary. Therefore, the actuation device 1 (160) can transition from a rest state, as depicted in FIG. 4A, to an actuated state as is depicted in FIGS. 4B and 4C. Alternatively, the communication electronics 410 can receive input from the wearable device 155 after an endpoint is detected. Therefore, the actuation device 1 (160) can transition from the actuated state back to the rest state. Although FIG. 4A depicts the communication electronics 410 as being located on the inner surface 422 of the actuation device 1 (160), in various embodiments, the communication electronics 410 can be located on another surface or internally within the housing 414 of the actuation device 1 (160).

The actuation device 1 (160) can include multiple actuating components 420a and 420b that are triggered when the communication electronics 410 of the actuation device 1 (160) receives the input indicating a need for a protective measure from the wearable device 155. As shown in FIG. 4A, a first actuating component 420a can be located in the housing 414 near or at the first end 412a whereas a second actuating component 420b can be located in the housing 414 near or at the second end 412b. In other embodiments, the actuating components 420 can be located within the housing 414 of the actuation device 1 (160) at other locations.

An actuating component 420 of the actuation device 1 (160) can provide one of a mechanical, chemical, or electrical inputs to actuate a stimulation structure 430. In other embodiments, input can be of a different energy modality such as an electromagnetic (e.g., magnetic) input. Specifically, in the embodiment shown in FIG. 4A, the actuating component 420 can provide an electrical input through the stimulation structure, also referred to as the electrodes 430. A first electrode 430a can be located at the first end 412a whereas a second electrode 430b can be located at the second end 412b. The electrodes 430 may be electrical contacts on a surface of the first end 412a and a surface of the second end 412b. Therefore, when actuated, an actuating component 420 can provide an input through the electrical contacts of the electrodes 430 in order to cause a gag reflex. Specifically, in reference to FIG. 4A, the actuating component 420 can be electrical hardware (e.g., battery, circuitry hardware) configured to provide an electrical input. The electrical contacts of the electrodes 430 can provide the electrical input (an applied voltage or an applied current) to the individual wearing the actuation device 1 (160).

In various embodiments, when residing in the mouth of the individual, the first end 412a and the second end 412b of the actuation device 1 (160) may each be in contact with a portion of the mouth of the individual. Specifically, the first end 412a and the second end 412b of the actuation device 1 (160) are in contact with one of the back of the tongue, the tonsils or areas around the tonsils, the uvula, or the back of the throat. Therefore, the electrode contacts of the electrodes 430 can similarly be in contact with one of the back of the tongue, the tonsils or areas around the tonsils, the uvula, or the back of the throat. The electrical input applied by the electrode 430 can trigger the glossopharyngeal nerve at the back of the individual's mouth to cause the gag reflex.

In various embodiments, the actuation device 1 (160) imparts a bilateral electrical stimulation through the two electrode contacts of the two electrodes 430. In some embodiments, a unilateral stimulation through a single electrode contact of a single electrode 430 is sufficient to cause a corresponding gag reflex in the individual.

Reference is now made to FIG. 4B, which illustrates a different embodiment of the actuation device 1 (160) for stimulating a gag reflex. Specifically, as shown in FIG. 4B, the actuation device 1 (160) is in a rest state. In this embodiment, the stimulation structure of the actuation device 1 (160) may be an inflatable structure 435 that causes a gag reflex in the individual. In various embodiments, this embodiment does not include electrode contacts of electrodes 430 as shown in FIG. 4A. In some embodiments, both the electrode contacts of the electrodes 430 and an inflatable structure 435 are included in the actuation device 1 (160) for stimulating a gag reflex.

The inflatable structure 435 may be coupled to the first end 412a of the actuation device 1 (160) through a first attachment point 416a. Furthermore, the inflatable structure 435 can be coupled to the second end 412b of the actuation device 1 (160) through a second attachment point 416b. Therefore, as shown in FIG. 4B, the inflatable structure 435 may directly traverse the distance between the first end 412a and the second end 412b of the actuation device 1 (160). In some embodiments, when in the rest state, the inflatable structure 435 can traverse along the inner surface 422 of the actuation device 1 (160). In other words, the inflatable structure 435 may follow the curvature of the inner surface 422 of the actuation device 1 (160) such that the inflatable structure 435 is less than a threshold distance away from the inner surface 422. Here, positioning the inflatable structure 435 close the inner surface 422 of the actuation device 1 (160) can prevent accidental stimulation of a gag reflex.

In various embodiments, the actuation device 1 (160) may include more than one inflatable structures 435. For example, a first inflatable structure 435 can be coupled at the first attachment point 416a to the first end 412a of the housing 414. Additionally, a second inflatable structure 435 can be coupled at the second attachment point 416b to the second end 412b of the housing 414. In some embodiments, when in the rest state, each of the first and second inflatable structure 435 may sit flush with the surface of the first end 412a and the surface of the second end 412b. For example, the first and second inflatable structure 435 can be stored in a cavity in the first end 412a and the second end 412b, respectively. Thus, this can prevent accidental stimulation of a gag reflex by the inflatable structures 435 when in a rest state.

FIG. 4C depicts the actuation device 1 (160) in an actuated state, in accordance with an embodiment. Here, the inflatable structure 435 shown in FIG. 4B changes its configuration to achieve an actuated inflated structure 440 (e.g., inflated). The actuated inflated structure 440 may remain coupled through the first attachment point 416a to the first end 412a of the housing 414 and through the second attachment point 416b to the second end 412b of the housing 414. When worn in the mouth of the individual, the actuated inflated structure 440 can physically contact one of the back of the tongue, the tonsils or areas around the tonsils, the uvula, or the back of the throat. As such, the actuated inflated structure 440 causes a gag reflex to occur in the individual.

In this embodiment, to achieve the actuated state, the actuating components 420 of the actuation device 1 (160) can cause the transition from the inflatable structure 435 shown in FIG. 4B to the actuated inflated structure 440 shown in FIG. 4C. As described above, the actuating components 420 can provide a chemical input. For example, each actuating component 420 can be configured to mix substances such as gasses, liquids, gels, and the like. Each substance can be stored within a cartridge that may be internal to the actuation device 1(160) or external to actuation device 1 (160). Mixing the substances causes a conversion of the substances into an expanded fluid, gas, or vapor that subsequently fills the inflatable structure 435. Altogether, the mixing of substances generates an expanded fluid, gas, or vapor that actuates (e.g., inflates) the inflatable structure 435 to achieve the actuated inflated structure 440 shown in FIG. 4C.

In some embodiments, the first actuating component 420a actuates a first inflatable structure 435 coupled to the first end 412a through attachment point 416a. Additionally, the second actuating component 420b actuates a second inflatable structure 435 coupled to the second end 412b through attachment point 416b. Therefore, the two inflatable structures may each actuate (e.g., inflate) and cause a gag reflex.

In various embodiments, the actuated inflated structure 440 (and the inflatable structure 435 when at rest) include vents 445 distributed throughout the actuated inflated structure 440 that enables a substance from within the actuated inflated structure 440 to escape. For example, the expanded fluid, gas, or vapor that actuated the inflatable structure 435 can escape through the vents 445 at a controlled rate depending on the size of the vents 445. As such, the actuated inflated structure 440 can return from the actuated state back to the inflatable structure 435 at a rest state. In another embodiment, the actuated inflated structure 440 includes a vent 445 that can be opened or closed given an electrical, chemical, or mechanical input. The input can be provided by the actuating component 420. As such, when the wearable device 155 detects that a protective measure is needed, the vent 445 can be closed when transitioning the actuation device 1 (160) from a rest state to an actuated state. Likewise, when the wearable device 155 detects an endpoint, vent 445 can be opened to transition the actuation device 1 (160) from an actuated state to a rest state.

Example Device for Stimulating a Valsalva-Like Maneuver

Figure 5A:
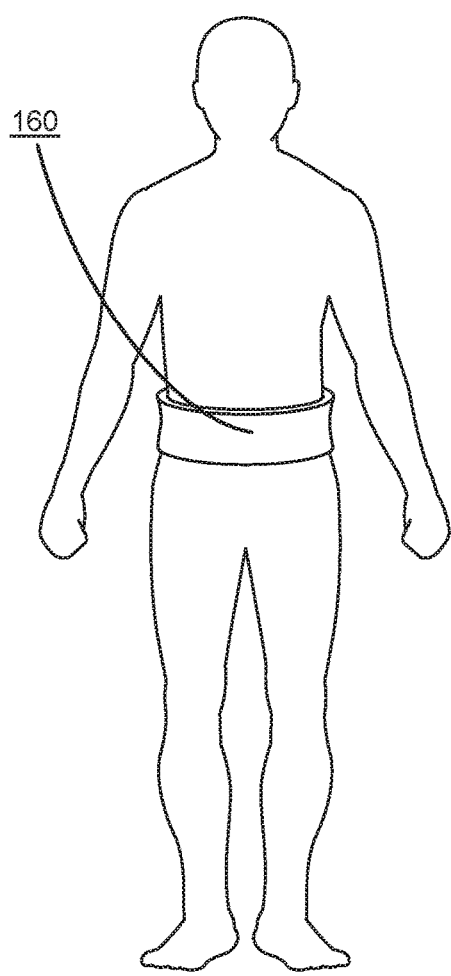
FIGS. 5A-5D each illustrates an example actuation device for inducing a valsalva-like maneuver, in accordance with an embodiment.
Figure 5B:
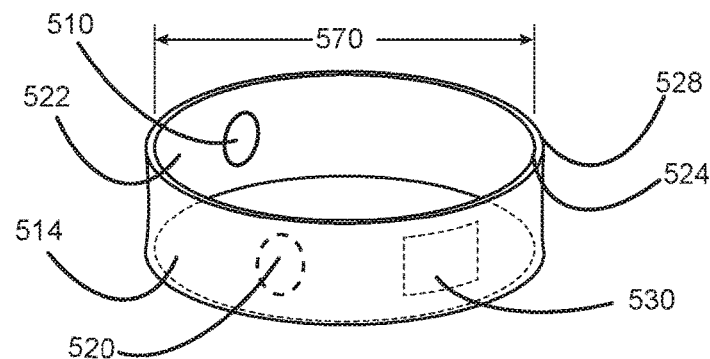
Figure 5C:
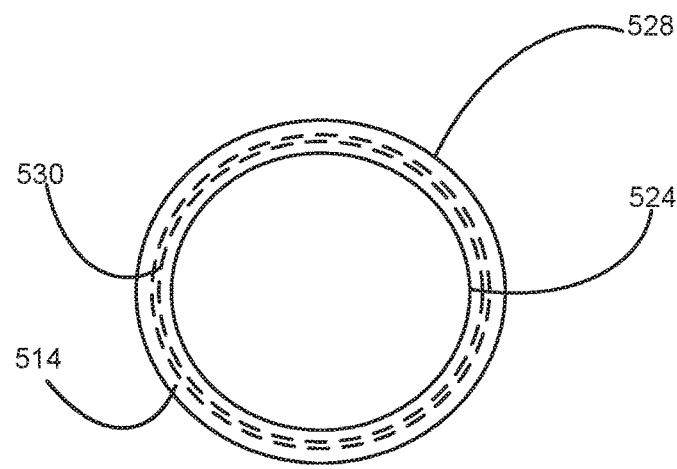

FIGS. 5A-C illustrates an example actuation device 1 (160) for inducing a valsalva-like maneuver, in accordance with an embodiment. For example, as depicted in FIG. 5A, the example actuation device 1 (160) is a waistband worn by an individual around his/her waist. In this embodiment, the waistband can be situated external to the individual's diaphragm. As such, when actuated, the waistband causes a valsalva-like maneuver by compressing the diaphragm and causing an increase in intraabdominal pressure and pressure within the thoracic cavity. In other embodiments, the example actuation device 1 (160) can be worn at any anatomical region between the chest and the waist. Although FIG. 5A depicts the waistband as fully encircling the individual's waist, in some embodiments, the waistband only encircles a portion of the individual. In some embodiments, the waistband encircles less than 50% of the individual's waist.

Referring to FIG. 5B, the actuation device 1 (160) may include communication electronics 510 and an actuating component 520 located within a housing 514 of the actuation device 1 (160). The actuation device 1 (160) may have an inner wall 524 and an outer wall 528. As such, the actuation device 1 (160) has inner diameter 570. Additionally, between the inner wall 524 and outer wall 528, the actuation device 1 (160) can include a stimulation structure such as an expandable cavity 530.

Figure 5D:
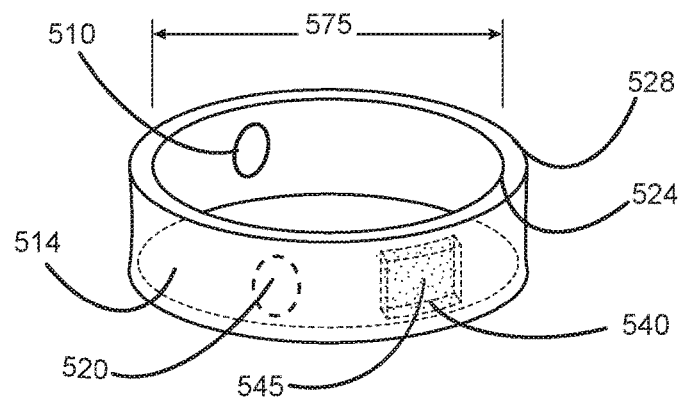

Similar to the communication electronics 410 described above in regards to FIG. 4, the communication electronics 510 of the actuation device 1 (160) can enable the actuation device 1 (160) to communicate with the wearable device 155 through one of Bluetooth, near field communication (NFC), WiFi, 2G, 3G, 4G, LTE, or other wireless or wired communication methods. Specifically, the communication electronics 510 of the actuation device 1 (160) receives input from the wearable device 155 after a protective measure is deemed necessary. Therefore, the actuation device 1 (160) can transition from a rest state, as depicted in FIG. 5B, to an actuated state as is depicted in FIG. 5D. Alternatively, the communication electronics 510 can receive input from the wearable device 155 after an endpoint is detected. Therefore, the actuation device 1 (160) can transition from the actuated state back to the rest state. In various embodiments, the communication electronics 510 can be located on the inner surface 522 of the actuation device 1 (160). In various embodiments, the communication electronics 510 can be located internally within the actuation device 1 (160).

The dimensions of the actuation device 1 (160) can be configured such that the actuation device 1 (160) be comfortably worn at the individual's waist when in the rest state. For example, the inner diameter 570 is designed so the inner wall 524 of the actuation device 1 (160) contacts, but does not constrict, the individual's waist. In various embodiments, the distance between the inner wall 524 and the outer wall 528 of the actuation device 1 (160) can range from 1 centimeter up to 10 centimeters when in the rest state.

The stimulation structure of the actuation device 1 (160), specifically an expandable cavity 530 as shown in FIG. 5B, is located between the inner wall 524 and the outer wall 528 of the actuation device 1 (160). In one embodiment, the expandable cavity 530 is only located within a portion of the actuation device 1 (160). As shown in FIG. 5B, the expandable cavity 530 may be a cavity that, when worn by the individual, is situated externally to the diaphragm. Therefore, actuation of the expandable cavity 530 would directly compress the diaphragm and cause a valsalva-like maneuver. FIG. 5C depicts a top-down view of another embodiment of the expandable cavity 530, as indicated by the dotted outlined structure, within the actuation device 1 (160) in the rest state. In this scenario, the expandable cavity 530 is concentrically located between the inner walls 524 and the outer walls 528 of the actuation device 1 (160).

Referring back to FIG. 5B, the actuating component 520 can cause the expandable cavity 530 to actuate (e.g., expand). As described above, the actuating component 520 can provide one or more of a mechanical, chemical, or electrical input to actuate the expandable cavity 530. As an example, each actuating component 530 can mix substances such as gasses, liquids, gels, and the like. The substances can be initially stored in a cartridge that is internal or external to the actuating device 1 (160). Mixing the substances causes a conversion of the substances into an expanded fluid, gas, or vapor that subsequently fills and expands the expandable cavity 530. The expansion of the expandable cavity 530 can happen in an instantaneous manner (e.g., less than 1 second). As such, the expandable cavity 530 can be actuated, as depicted in FIG. 5D.

FIG. 5D depicts the actuation device 1 (160) in an actuated state, in accordance with an embodiment. Generally, the actuated cavity 540 can cause the actuation device 1 (160) to alter its configuration and cause a valsalva-like maneuver. The distance between the inner wall 524 and the outer wall 528 can be increased in the actuated state as compared to the corresponding distance when in the rest state. Additionally, the inner diameter 575 of the actuation device 1 (160) can be reduced in the actuated state as compared to the inner diameter 570 of the actuation device 1 (160) when in the rest state. Although FIG. 5C depicts a reduced inner diameter 575 across the entire inner wall 524, in various embodiments, a reduced inner diameter 575 only occurs in a portion of the actuation device 1 (160). For example, if the expandable cavity 530 is within a portion of the actuation device 1 (160) as shown in FIG. 5B, then the reduced inner diameter 575 of the actuation device 1 (160) can correspond to the location of the inner wall 524 where the actuated cavity 540 is located.

In various embodiments, the actuated cavity 540 also include vents 545 distributed throughout the actuated cavity 540. The vents 545 may be connected through the inner wall 524 or outer wall 528 such that a substance from within the actuated cavity 540 can escape out to the environment. For example, the expanded fluid, gas, or vapor that previously actuated the expandable cavity 530 can escape through the vents 545 at a controlled rate depending on the size of the vents 545. As such, the actuated cavity 540 can return from the actuated state back to the expandable cavity 530 at a rest state. In another embodiment, the actuated cavity 540 includes a vent 545 that can be opened or closed given an electrical, chemical, or mechanical input. The input can be provided by the actuating component 520. As such, when the wearable device 155 detects that a protective measure is needed, the vent 545 can be closed when transitioning the actuation device 1 (160) from a rest state to an actuated state. Likewise, when the wearable device 155 detects an endpoint, vent 545 can be opened to transition the actuation device 1 (160) from an actuated state to a rest state.

Example Computing System of the System Environment

Figure 6:
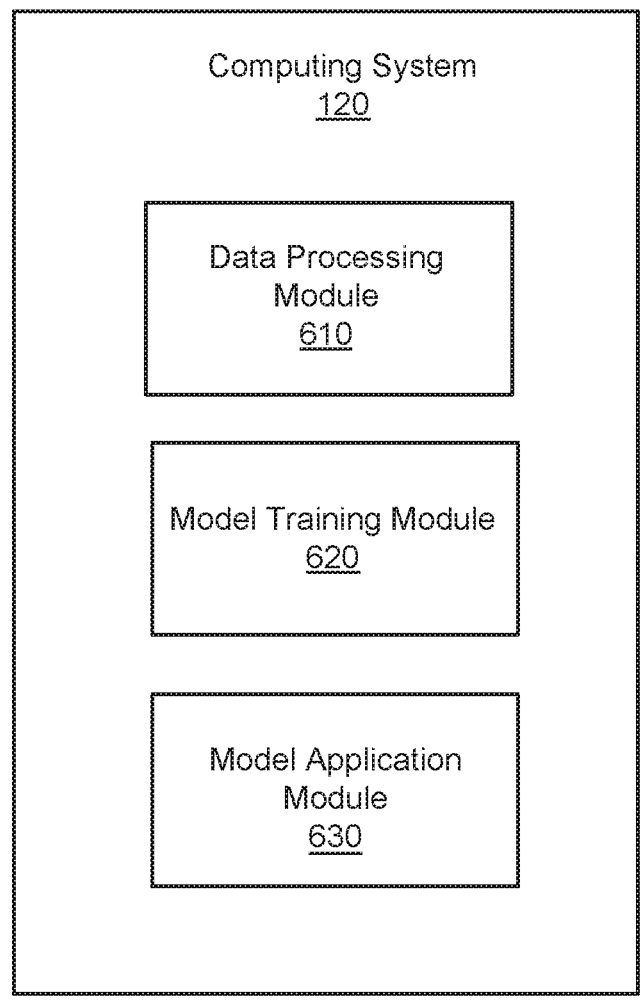
FIG. 6 illustrates an example block diagram depicting the system architecture of a computing system, in accordance with an embodiment.

FIG. 6 illustrates an example block diagram depicting the system architecture of a computing system 120, in accordance with an embodiment. The computing system 120 may include a data processing module 610, a model training module 620, and a model application module 630.

The data processing module 610 receives gathered sensor data. In one embodiment, the data processing module 610 receives gathered sensor data from the remote sensors 125 and/or from the sensors 180 of the wearable device 155. As previously described, the gathered sensor data can include orientation and/or position of the wearable device 155 as well as data corresponding to an occurring or impending collision (e.g., speed of collision). Additionally, if the system environment 100 includes multiple brain injury reduction systems 150, then the data processing module 610 can receive gathered sensor data corresponding to the relative location of a first wearable device from a first brain injury reduction system 150 to a second wearable device from a second brain injury reduction system 150. In this scenario, the computing system 120 can analyze collisions that may occur as a result of two or more wearable devices 155. This can be particularly relevant in analyzing collisions in a competitive sporting event such as a football game.

In one embodiment, the data processing module 610 may preprocess the gathered data such that the data can be subsequently analyzed. For example, the data processing module 610 can apply a filter (e.g., low pass, bandpass, or high pass) to eliminate noise in the gathered data. The processed data is then provided to either the model training module 620 for training a machine-learning model or to the model application module 630 for determination of whether a protective measure is needed.

The model training module 620 executes a machine learning algorithm using the received processed data as training data to train a machine learning model. Machine learning techniques for training the machine-learning model may be one of random forests, neural networks, naïve Bayes, support vector machines, short-term memory networks, logistic regression, bagged trees, decision trees, boosted trees and machine learning used in HIVE™ frameworks, in different embodiments.

More specifically, the computing system 120 may train a classification model such that the classification model outputs one of two possible outputs. For example, given the training data, the classification model is trained by using, as output labels, a designation of whether a protective measure is needed or not. In some embodiments, a classification model is trained specifically for an individual. In other words, a classification model can be trained to consider the personal tendencies and behavior of an individual that may change the susceptibility of the individual to brain injury. In other embodiments, the model training module 620 trains a classification model for a group of individuals that is specific for a demographic (e.g., elderly individuals) or any other characteristic (e.g., for a particular football position such as a running back, a quarterback, a linesman, and the like).

The model application module 630 applies a trained machine-learning model to newly received sensor data that corresponds to a currently occurring or impending collision. Thus, the trained machine learning model evaluates whether a protective measure needs to be performed in response to the gathered data. If a protective measure is needed, the computing system 120 provides the evaluation to the brain injury reduction system 150. Therefore, the wearable device 155 of the brain injury reduction system 150 can execute the protective measure. In some embodiments, the computing system 120 provides the trained machine learning model to the brain injury reduction system 150 such that when an occurring or impending collision is detected, the wearable device 155 can rapidly determine whether a protective measure is to be provided by applying the trained machine learning model.

Providing a Protective Measure for Reducing Brain Injury

Figure 7:
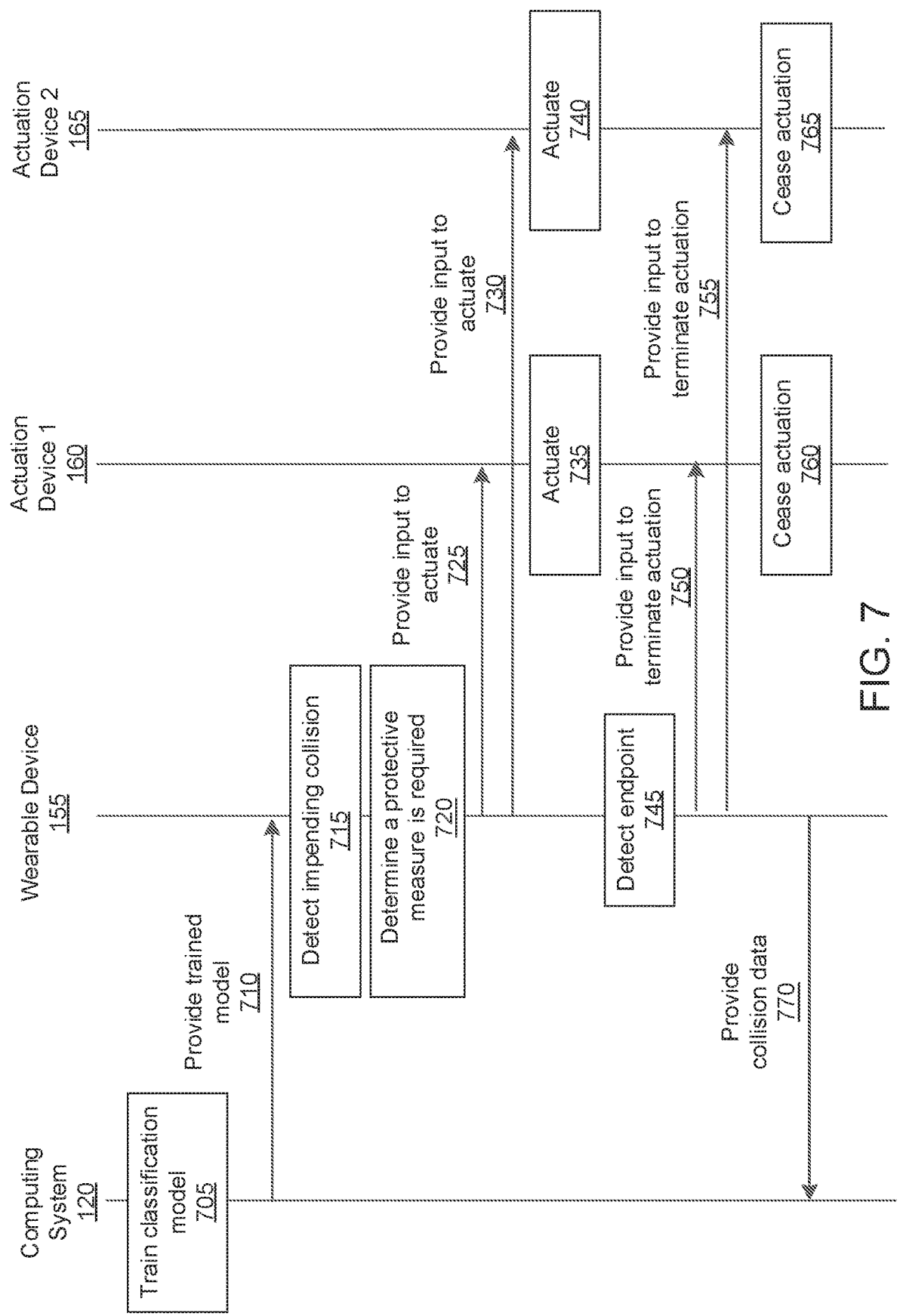
FIG. 7 illustrates an example interaction diagram for providing a protective measure for reducing brain injury in an individual, in accordance with an embodiment.

FIG. 7 illustrates an example interaction diagram for providing a protective measure for reducing brain injury in an individual, in accordance with an embodiment. In some embodiments, the process of providing a protective measure includes the wearable device 155 and one of the actuation devices 160 or 165. In various embodiments, the process need not include the computing system 120 such that detection of an impending collision by the wearable device 155 is performed autonomously.

Initially, a computing system 120 of the system environment 100 may train 705 a classification model that receives data corresponding to an occurring or impending collision as inputs, and outputs a classification as to whether a protective measure is to be provided. Generally, the classification model can be trained on training data that is derived from prior collisions. For example, training data may include data that is specific to an individual that was involved in the prior collision including, but not limited to, the orientation and/or position of the individual, the speed at which the individual was traveling, unique characteristics of the individual (e.g., reaction time), and the like. Therefore, a trained classification model may be specifically trained for a particular individual such that determination of whether a protective measure is required is specifically tailored for the individual.

As depicted in FIG. 7, the trained classification model is provided 710 to the wearable device 155 of the brain injury reduction system 150. Therefore, when the wearable device 155 detects 715 an impending collision, the wearable device 155 can rapidly determine 720 that a protective measure is required by applying the data corresponding to the impending collision to the trained classification model.

In another embodiment, the trained classification model is maintained by the computing system 120. Therefore, when the wearable device 155 detects 715 an impending collision, the data corresponding to the impending collision is transmitted to the computing system 120 to determine whether a protective measure is required. As such, the computing system 120 can provide an input to the wearable device 155 as to whether a protective measure is to be performed.

Once the wearable device 155 determines or receives instructions that a protective measure is required, the wearable device 155 provides 725 an input to an actuation device 1 (160) and provides 730 an input to an actuation device 2 (165). This input may be provided through wired or wireless communication technology (e.g., Bluetooth, NFC, WiFi, LTE, and the like). In some embodiments, the wearable device 155 only provides 730 an input to actuation device 1 (160) to maintain intracranial venous pressure by reducing venous drainage through the PVP.

Each of actuation device 1 (160) and actuation device 2 (165) actuate 735 and 740, thereby reducing venous drainage through the PVP and the IJVs, respectively. As previously described, actuation of actuation device 1 (160) may involve stimulating a gag reflex or a valsalva-like maneuver using actuation device 1 (160). Additionally or alternatively, actuation of actuation device 2 (165) may involve external compression of the IJVs through physical structures of the actuation device 2 (165).

The wearable device 155 detects 745 an endpoint. For example, a detected endpoint may be detection of collisions. The wearable device 155 can record data corresponding to the detected collisions. As another example, a detected endpoint may be a pre-determined duration of time after the protective measure is provided. In some embodiments, the endpoint is a detected one or more collisions followed by a pre-determined duration after the detected one or more collisions. The wearable device 155 provides 750 input to the actuation device 1 (160) to terminate actuation. Alternatively or additionally, the wearable device 155 provides 755 input to the actuation device 2 (165) to terminate actuation. As such, the actuation device 1 (160) and/or the actuation device 2 (165) return to a rest state in response to the input. In some embodiments, each of the actuation device 1 (160) and actuation device 2 (165) return to an original configuration. Therefore, the individual need not endure a prolonged period of the protective measure after the collision has occurred.

In various embodiments, the wearable device 155 can provide 770 recorded collision data (e.g., orientation of the individual, imparted force, speed of collision, and the like) to the computing system 120. As such, the computing system 120 can continue to train the classification model 705 to more accurately determine when a protective measure for the individual is required.

Additional Embodiment Considerations

Throughout this specification, as used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

The term "housing" or "means for housing," as used throughout, may refer to any holder or structure that houses all or a portion of a component of the system, such as an actuation device, a sensor, or both. The term "actuation device" or "means for actuating" as used throughout, may refer to any device or entity (including mechanical, electrical, or chemical actuation devices) that interacts with the body or otherwise operates to cause a response that prevents or reduces outflow of venous drainage from the PVP, IJVs, or both (or other component via which venous drainage from the intracranial compartment occurs). The term "sensing device," "sensor," "means for detecting" or "means for sensing," as used throughout, may refer to any device capable of sensing or detecting an effect or occurrence that indicates an impending or occurring collision.

Finally, as used herein any reference to "one embodiment," "some embodiments," or "various embodiments" means that a particular element, feature, structure, or characteristic described in connection with the embodiment is included in at least one embodiment. The appearances of the phrase "in one embodiment" in various places in the specification are not necessarily all referring to the same embodiment.

Upon reading this disclosure, those of skilled in the art will appreciate still additional alternative structural and functional designs for propeller blades as disclosed from the principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement and details of the apparatus disclosed herein without departing from the spirit and scope defined in the appended claims.

What is claimed is:

1. A system for reducing a severity of a brain injury incurred by an individual due to a change in head acceleration of the individual, the system comprising:
   a wearable sensing device comprising:
      a wearable housing configured to be worn on the body of the individual, and
      one or more sensors positioned on or within the wearable housing to detect an occurring or impending event that would result in the change in head acceleration;

a first wearable actuation device comprising:
  a first plurality of electrodes configured to stimulate one or more abdominal muscles or one or more abdominal nerves of the individual when an electric signal is applied to the plurality of electrodes;
a second wearable actuation device comprising:
a second plurality of electrodes configured to stimulate nerves of the individual to cause glottis closure in the individual or to cause a gag reflex in the individual; and
communication electronics on or within at least one of the wearable sensing device, the first wearable actuation device, and the second wearable actuation device, the communication electronics configured to:
  transmit, subsequent to detection of the occurring or impending event by the one or more sensors of the wearable sensing device, a first input to the first wearable actuation device and the second wearable actuation device, the first input triggering an actuated state of the first wearable actuation device and the second wearable actuation device, during which the first wearable actuation device applies the electric signal to the first plurality of electrodes and the second wearable actuation device applies the electric signal to the second plurality of electrodes, and
  after a duration of time from transmitting the first input, transmit a second input to the first wearable actuation device and the second wearable actuation device, the second input causing the actuated state to cease and to transition into a rest state of the first wearable actuation device and the second wearable actuation device, during which the first wearable actuation device no longer applies the electric signal to the first plurality of electrodes and the second wearable actuation device no longer applies the electric signal to the second plurality of electrodes.

2. The system of claim 1, wherein the wearable housing is a housing of a helmet.

3. The system of claim 1, wherein the second plurality of electrodes of the second wearable actuation device are configured to transcutaneously stimulate the laryngeal nerves or the glossopharyngeal nerve of the individual when the electric signal is applied to the second plurality of electrodes.

4. The system of claim 1, wherein the second wearable actuation device comprises:
  a first end comprising a first electrode;
  a second end comprising a second electrode;
  an external cavity configured to receive teeth of the individual; and
  an actuating component for providing an electric input to the glossopharyngeal nerve of the individual through the first electrode of the first end and the second electrode of the second end to cause the gag reflex.

5. The system of claim 1, further comprising:
  a third wearable actuation device comprising:
  a first end;
  a second end; and
  a housing configured to be circumferentially positioned around a neck of the individual, the housing comprising a first extendable protrusion and a second extendable protrusion,
  wherein the first extendable protrusion of the third wearable actuation device is configured to compress a left internal jugular vein when in the actuated state, and
  wherein the second extendable protrusion is configured to compress a right internal jugular vein of the individual when in the actuated state.

6. The system of claim 5, wherein the first extendable protrusion of the third wearable actuation device is located on an inner surface of the third wearable actuation device, and wherein the second extendable protrusion of the third wearable actuation device is located on an inner surface of the third wearable actuation device.

7. The system of claim 5, wherein the housing of the third wearable actuation device has a larger curvature in the actuated state than when in the rest state.

8. The system of claim 1, further comprising:
  a computing system in communication with the wearable sensing device of the system, the computing system configured to apply a trained machine-learning model to data corresponding to the occurring or impending event detected by the one or more sensors of the wearable sensing device to determine the first input.

9. A method for reducing severity of a brain injury incurred by an individual due to a change in head acceleration of the individual, the method comprising:
  detecting an occurring or impending event to a head of the individual;
  subsequent to detection of the occurring or impending event, providing a first input to a first wearable actuation device comprising a first plurality of electrodes configured to stimulate one or more abdominal muscles or one or more abdominal nerves of the individual when an electric signal is applied to the plurality of electrodes and to a second wearable actuation device comprising a second plurality of electrodes configured to stimulate nerves of the individual to cause glottis closure in the individual or to cause a gag reflex in the individual, the first input triggering an actuated state of the first wearable actuation device and the second wearable actuation device, during which the first wearable actuation device applies the electric signal to the first plurality of electrodes and the second wearable actuation device applies the electric signal to the second plurality of electrodes; and
  after a duration of time from providing the first input, providing a second input to the first wearable actuation device and the second wearable actuation device, the second input causing the actuated state to cease and to transition into a rest state of the first wearable actuation device and the second wearable actuation device, during which the first wearable actuation device no longer applies the electric signal to the first plurality of electrodes and the second wearable actuation device no longer applies the electric signal to the second plurality of electrodes.

10. The method of claim 9, wherein after a duration of time, providing the second input to the first wearable actuation device and the second wearable actuation device comprises:
  detecting a subsequent event to the head of the individual after providing the first input to the first wearable actuation device and the second wearable actuation device; and
  responsive to detecting the subsequent event,
    providing the second input to the first wearable actuation device and the second wearable actuation device.

11. The method of claim 9, wherein after a duration of time, providing the second input to the first wearable actuation device and the second wearable actuation device comprises:
  detecting that a duration of time has elapsed;

responsive to detecting that the duration of time has elapsed, providing the second input to the first wearable actuation device and the second wearable actuation device.

12. The method of claim 9, further comprising:
responsive to detecting the occurring or impending event, determining whether a protective measure is required based on data corresponding to the occurring or impending event, and
wherein the first input is provided to the first wearable actuation device and the second wearable actuation device responsive to determining that the protective measure is required.

13. The method of claim 12, wherein the data corresponding to the occurring or impending event comprises a position of the individual relative to an object with which that individual is or will collide.

14. The method of claim 12, wherein determining whether a protective measure is required comprises applying the data corresponding to the occurring or impending event as an input to a trained machine-learning model.

15. The method of claim 9, wherein detecting the occurring or impending event to a head of the individual comprises detecting a change in one of air pressure waves or electromagnetic waves.

16. A system for reducing a severity of a brain injury incurred by an individual due to a change in head acceleration of the individual, the system comprising:
one or more means for detecting an occurring or impending event that would result in the change in head acceleration; one or more means for,
subsequent to detection of the occurring or impending event,
actuating a first wearable actuation device to apply an electric signal to a first plurality of electrodes that are configured to stimulate one or more abdominal muscles or one or more abdominal nerves of the individual when an electric signal is applied to the plurality of electrodes, and
one or more means for,
subsequent to detection of the occurring or impending event,
actuating a second wearable actuation device to apply an electric signal to a second plurality of electrodes that are configured to stimulate nerves of the individual to cause glottis closure in the individual or to cause a gag reflex in the individual, and
after a duration of time from actuating the first wearable actuation device and the second wearable actuation device, causing a rest state of the first wearable actuation device and the second wearable actuation device, during which the first wearable actuation device no longer applies the electric signal to the first plurality of electrodes and the second wearable actuation device no longer applies the electric signal to the second plurality of electrodes.

17. The system of claim 16, wherein the one or more means for detecting the occurring or impending event comprise one or more sensors positioned on or within a housing configured to be worn on the body of the individual.

18. The system of claim 16, wherein the plurality of electrodes are positioned on or within a housing of the first wearable actuation device.

19. The system of claim 16, further comprising one or more means for actuating a third wearable actuation device configured to compress internal jugular veins of the individual.

20. The system of claim 1, further comprising a processor and a memory in at least one of the wearable sensing device, the first wearable actuation device, and the second wearable actuation device, the memory storing code that when executed by the processor causes the processor to:
receive data captured by the one or more sensors of the wearable sensing device, the data indicating detection of an occurring or impending event;
determine whether a protective measure for the individual is needed based on the received data; and
in response to a determination that the protective measure is needed, instruct the communication electronics to transmit the first input to the first wearable actuation device and the second wearable actuation device.

21. The system of claim 20, wherein the memory further stores code that when executed by the processor causes the processor to:
after the communication electronics is instructed to transmit the first input to the first wearable actuation device and the second wearable actuation device, determine whether the protective measure for the individual is not needed any more; and
in response to a determination that the protective measure is not needed any more, instruct the communication electronics to transmit the second input to the first wearable actuation device and the second wearable actuation device.

22. The system of claim 21, wherein the code that when executed by the processor causes the processor to determine whether the protective measure for the individual is not needed any more comprise code that when executed by the processor causes the processor to:
determine whether a threshold duration of time has elapsed since the detection of the occurring or impending event.

23. The system of claim 21, wherein the code that when executed by the processor causes the processor to determine whether the protective measure for the individual is not needed any more comprise code that when executed by the processor causes the processor to:
receive second data captured by the one or more sensors of the wearable sensing device, the second data indicating detection of a second occurring or impending event; and
determine whether the protective measure for the individual is not needed any more based on the received second data.

24. The system of claim 16, wherein the one or more means for actuating the second wearable actuation device comprise one or more means for actuating the second plurality of electrodes configured to stimulate the laryngeal nerve or the glossopharyngeal nerve of the individual.

25. The system of claim 24, wherein the second wearable actuation device comprises:
a first end comprising a first electrode of the plurality of additional electrodes;
a second end comprising a second electrode of the plurality of additional electrodes;
an external cavity configured to receive teeth of the individual; and
an actuating component for providing an electric input to the glossopharyngeal nerve of the individual through the first electrode of the first end and the second electrode of the second end to cause the gag reflex.

26. The system of claim 17, wherein the one or more means for detecting one of the occurring or impending event further comprise:
a computing system in communication with the one or more sensors, the computing system configured to apply a trained machine-learning model to data corresponding to the occurring or impending event detected by the one or more sensors to determine an input to the first wearable actuation device and the second wearable actuation device, the input instructing the first wearable actuation device to apply the electric signal to the first plurality of electrodes and instructing the second wearable actuation device to apply the electric signal to the second plurality of electrodes.

* * * * *